(12) United States Patent
Abe et al.

(10) Patent No.: US 8,501,972 B2
(45) Date of Patent: Aug. 6, 2013

(54) SOLID FATTY ALKYL ESTER SULFONATE METAL SALT AND METHOD FOR PRODUCING POWDER THEREOF WITH SHARP PARTICLE SIZE DISTRIBUTION

(75) Inventors: Yutaka Abe, Tokyo (JP); Naoki Nakamura, Tokyo (JP); Takao Matsuo, Tokyo (JP); Daisuke Negishi, Tokyo (JP); Hiroyuki Masui, Tokyo (JP); Toru Yoshii, Tokyo (JP); Nobukazu Shogase, Tokyo (JP); Masahiko Matsubara, Tokyo (JP)

(73) Assignee: Lion Corporation, Tokyo (JP)

( * ) Notice: Subject to any disclaimer, the term of this patent is extended or adjusted under 35 U.S.C. 154(b) by 286 days.

(21) Appl. No.: 12/739,255

(22) PCT Filed: Oct. 22, 2008

(86) PCT No.: PCT/JP2008/069131
§ 371 (c)(1),
(2), (4) Date: Aug. 13, 2010

(87) PCT Pub. No.: WO2009/054406
PCT Pub. Date: Apr. 30, 2009

(65) Prior Publication Data
US 2010/0305343 A1 Dec. 2, 2010

(30) Foreign Application Priority Data

Oct. 22, 2007 (JP) ................................. 2007-274308
Oct. 22, 2007 (JP) ................................. 2007-274309

(51) Int. Cl.
*C11D 1/28* (2006.01)
*C11D 17/06* (2006.01)

(52) U.S. Cl.
USPC .................. 554/97; 554/85; 554/88; 554/96; 510/446; 510/414; 510/454

(58) Field of Classification Search
None
See application file for complete search history.

(56) References Cited

U.S. PATENT DOCUMENTS 3,969,375 A * 7/1976 Okumura et al. ............... 554/97
4,874,552 A 10/1989 Richtler et al.
2006/0160717 A1 7/2006 Itakura et al.

FOREIGN PATENT DOCUMENTS

JP 62-298570 12/1987

(Continued)

OTHER PUBLICATIONS

JP 07-247259, KAO, Corp, Production of Alpha-Sulfofatty acid alkyl ester salt, 1995, English Translation, 9 pages.*
Stirton, a.J., et al., Salts of Alkyl Esters of alpha-Sulfopalmitic and alpha-sulfosteric acids, 1965, Journal of the American Oil Chemists' Society, vol. 42, pp. 1078-1081.*
JP2006-161002: Lion Corp., High concentration alpha-sulfofatty acid alkyl ester salt containign particle and method for producing the same and detergent, 2006, English translation of Specification, (28 pages).*

(Continued)

*Primary Examiner* — Yate K Cutliff
(74) *Attorney, Agent, or Firm* — Nath, Goldberg & Meyer; Joshua B. Goldberg; Megan B. Doughty

(57) ABSTRACT

A solid fatty acid alkyl ester sulfonate metal salt is disclosed having an endothermic peak area between 50° C. and 130° C. of 50% or more relative to the whole endothermic peak area between 0° C. and 130° C. when determined using a differential scanning calorimter. A method for producing a fatty acid alkyl ester sulfonate metal salt powder is also disclosed, including a step of pulverizing the solid fatty acid alkyl ester sulfonate metal salt in a pulverizer, with the internal temperature of the pulverizer being adjusted to 30° C. to 50° C.

16 Claims, 8 Drawing Sheets

FOREIGN PATENT DOCUMENTS

| | | | |
|---|---|---|---|
| JP | 07-247259 | * | 9/1995 |
| JP | 10-298159 A | | 11/1998 |
| JP | 2003-82395 A | | 3/2003 |
| JP | 2003-105396 A | | 4/2003 |
| JP | 2004-210807 A | | 7/2004 |
| JP | 2006-161002 A | | 6/2006 |
| WO | WO 2004/111166 A1 | | 12/2004 |
| WO | 2007/108418 A1 | | 9/2007 |

OTHER PUBLICATIONS

International Search Report for related international application No. PCT/JP2008/069131, report dated Jan. 9, 2009.

JPO Office Action, mailed on Jun. 5, 2013, for Japanese Patent Application No. 2009-538230, three (3) pages in Japanese.

* cited by examiner

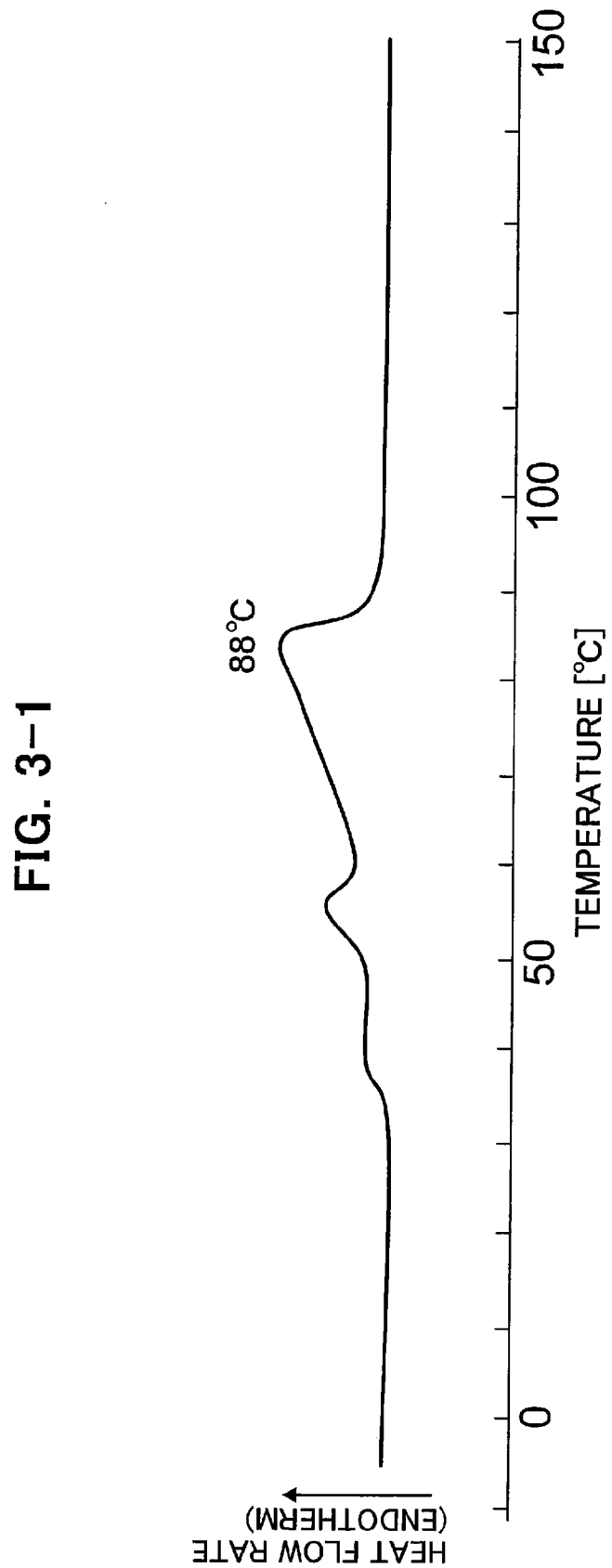

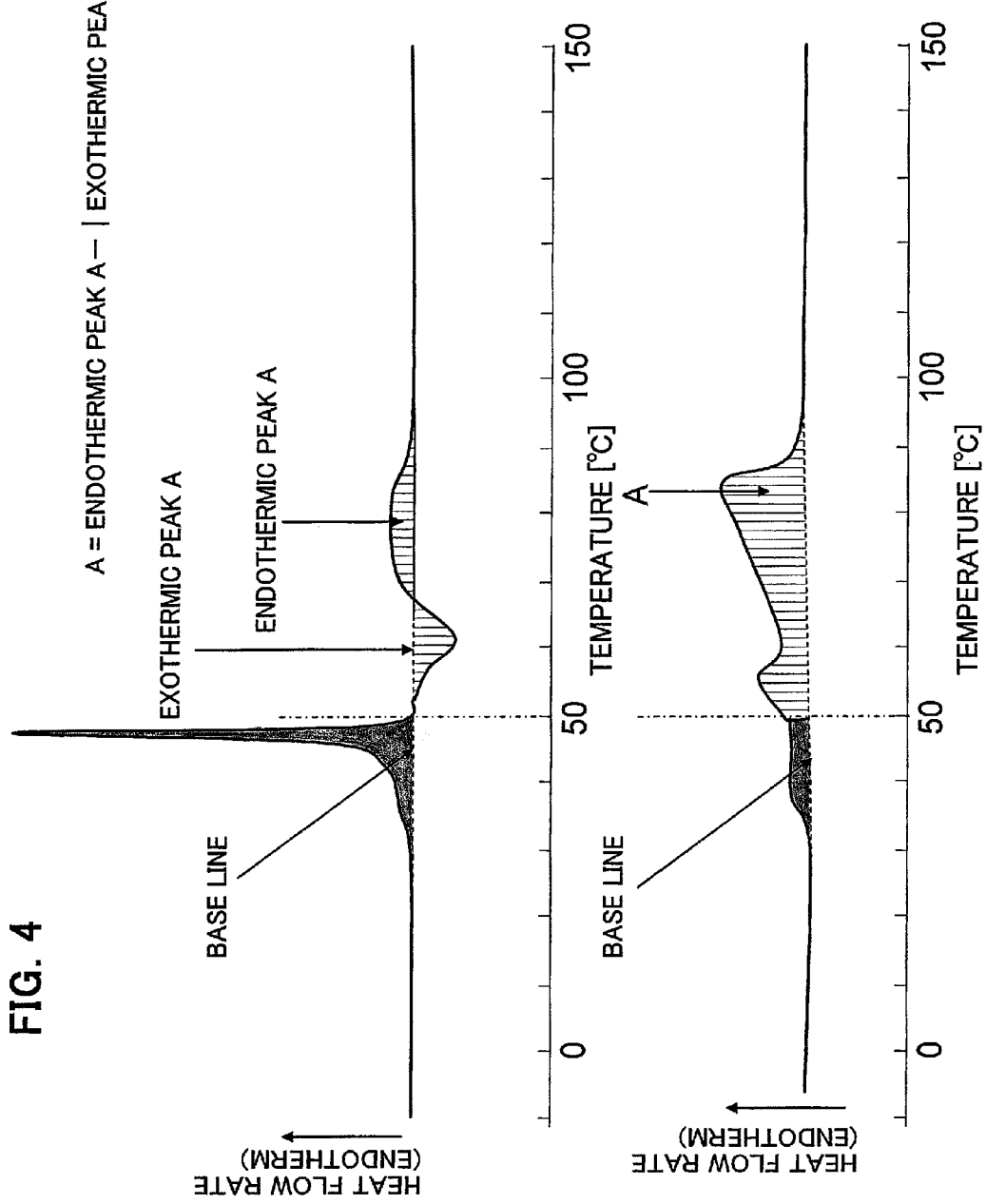

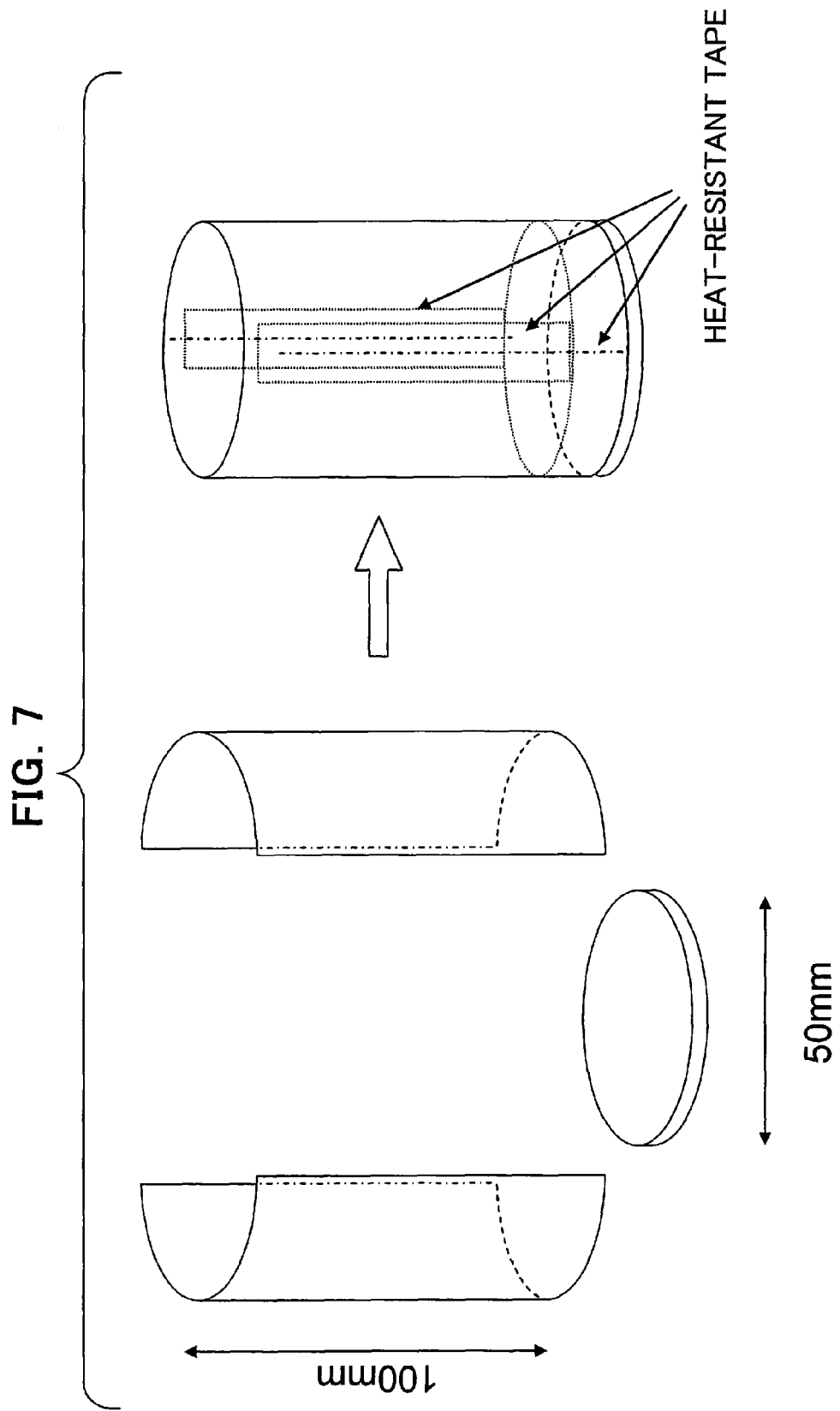

SOLID FATTY ALKYL ESTER SULFONATE METAL SALT AND METHOD FOR PRODUCING POWDER THEREOF WITH SHARP PARTICLE SIZE DISTRIBUTION

CROSS-REFERENCE TO RELATED APPLICATION

This is a 35 USC §371 National Stage Application of International Patent Application No. PCT/JP2008/069131 filed on Oct. 22, 2008, which claims priority under the Japan Convention to Japanese Patent Application No. JP 2007-274308 and JP 2007-274309, filed on Oct. 22, 2007.

FIELD OF THE DISCLOSURE

Technical Field

This disclosure relates to a solid fatty acid alkyl ester sulfonate metal salt suitable as the raw material for granular detergents for clothes and the like and a method for producing the same, and a method for producing a fatty acid alkyl ester sulfonate metal salt powder suitable as the raw material for the granular detergents for clothes and the like, a fatty acid alkyl ester sulfonate metal salt powder obtainable by the above-mentioned production method, and a granular detergent composition for textile goods or the dishes, containing the above-mentioned powder.

BACKGROUND OF THE DISCLOSURE

The fatty acid alkyl ester sulfonate metal salt (hereinafter also referred to as "MES") is widely used as a surfactant for producing granular detergent compositions for clothes. A variety of production methods for granular detergent compositions are known, and dry-blending of the MES powder with another surfactants, builders and the like, spray-drying and the like are typical examples of the production method.

When the MES is subjected to dry-blending, the MES in a paste form is once concentrated into a solid form, and the solid is then crushed. When a granular detergent composition is produced by the spray drying method using the MES, it is common practice to form a detergent slurry by mixing the MES in a paste form containing a considerable water content with the builders and the like. In such cases, dry-blending of powders or preparation of detergent slurry is often carried out at a place far from the site where the MES paste has been produced. Namely, it may be required to transport the MES in a paste form not only within Japan, but also to the foreign countries. The cost of transporting the MES in a paste form is high. The MES in the form of a concentrate can be transported more economically. There are some known methods for concentrating the MES (Japanese Patent Unexamined Publication (hereinafter referred to as "JP Kokai") No. 2004-210807, National publication of PCT application 2004/111166, JP Kokai No. 2003-105396, and JP Kokai No. 2003-82395).

When the concentrate in a solid state is transported, however, the solid will tend to produce cakes under the circumstances of heavy load or high temperature, which makes it difficult to take the concentrate out of the container. In addition, when the caking takes place in the concentrate, the pulverizing process or the process of reconstituting to a paste will be hindered if the process is carried out at the place where the concentrate has been transferred. This means deterioration of the handling properties.

To produce the granular detergent composition, which is constructed of a surfactant, zeolite, alkali chemical, dye and the like, a pulverizing step is often provided for the purpose of sizing to improve the fluidity and the appearance after the granulation step.

The fatty acid alkyl ester sulfonate metal salt (MES) is widely used as a surfactant for constituting the granular detergent composition. When the MES powder is prepared, the pulverizer is operated, generally with cold air of less than 30° C. being blown into the pulverizer to prevent the powder from adhering to the pulverizer (for example, as in National publication of PCT application 2004/111166).

However, the MES powder obtainable by the above-mentioned method shows a broad particle size distribution including high amounts of coarse powders and fine powders. With high content of coarse powders, the problem of low water solubility is produced. High content of fine powders also produces the problem of low water solubility because of the formation of cakes during the storage.

In contrast to this, the powder with a narrow particle size distribution, i.e., containing smaller amounts of coarse powders and fine powders can reduce the occurrence of the above-mentioned problems. In addition to the above, the powder with a narrow particle size distribution can be blended with inorganic powders such as zeolite and the like without classification, which is considered to be industrially advantageous.

SUMMARY OF THE DISCLOSURE

In the production of a granular detergent composition, the increase in the internal temperature of the pulverizer during the step of pulverizing the MES flakes may unfavorably cause the adhesion of the ground powders to the inside of the pulverizer. In light of this, an indispensable condition for pulverizing the MES flakes is to control the internal temperature to 30° C. or less, and therefore, the problem of scattering particle size distribution has remained. Conversely, when the pulverization is carried out at high internal temperature of the pulverizer by heating the flakes, the air flow or the pulverizer itself in order to obtain the MES powder with a narrow particle size distribution, there has also remained a problem that the powders are getting so sticky as to adhere to the pulverizer.

Accordingly, an object of the invention is to provide a method for producing a fatty acid alkyl ester sulfonate metal salt powder with a narrow particle size distribution, which can be prevented from adhering to the pulverizer.

As a result of the studies intensively made by the inventors of the invention, it has been found that a particular treatment can convert the fatty acid alkyl ester sulfonate metal salt into a novel crystalline state with a stable structure resistant to caking.

Accordingly, the present invention provides a solid fatty acid alkyl ester sulfonate metal salt, characterized in that the endothermic peak area between 50° C. and 130° C. is 50% or more relative to the whole endothermic peak area between 0° C. and 130° C. when determined using a differential scanning calorimeter.

Also, the invention provides a method for producing the above-mentioned solid fatty acid alkyl ester sulfonate metal salt, comprising the step of:

(I) maintaining a metastable solid fatty acid alkyl ester sulfonate metal salt at 30° C. or more for at least 48 hours under pressure of 20,000 Pa or less, (II) melting a metastable solid fatty acid alkyl ester sulfonate metal salt and maintaining the obtained melt for 5 minutes or more at a temperature from the melting point of the metastable solid fatty acid alkyl ester sulfonate metal salt to the melting point of the solid fatty acid alkyl ester sulfonate metal salt, or (III) melting a metastable solid fatty acid alkyl ester sulfonate metal salt and applying a shearing force to the obtained melt at a shear rate of 100 (1/s) or more at a temperature from the melting point of the metastable solid fatty acid alkyl ester sulfonate metal salt to 80° C.

Further, it has been discovered from the intensive studies by the inventors that when a particular crystal form of MES is subjected to pulverizing, the pulverizing operation can be performed at high temperatures without generating the problem of adhesion of powder to the pulverizer, so that the MES powder with a sharp particle size distribution can be obtained.

Namely, the present invention provides a method for producing a fatty acid alkyl ester sulfonate metal salt powder, comprising the step of pulverizing a solid fatty acid alkyl ester sulfonate metal salt at the internal temperature of a pulverizer of 30° C. or more and 50° C. or less, wherein the solid fatty acid alkyl ester sulfonate metal salt has an endothermic peak area between 50° C. and 130° C. of 50% or more relative to the whole endothermic peak area between 0° C. and 130° C. when determined using a differential scanning calorimeter.

The present invention also provides a fatty acid alkyl ester sulfonate metal salt powder obtained by the above-mentioned production method.

The invention provides a granular detergent composition for textile goods or the dishes, characterized by containing the above-mentioned fatty acid alkyl ester sulfonate metal salt powder.

According to the invention, it is possible to obtain a solid fatty acid alkyl ester sulfonate metal salt that is resistant to caking even though the solid material is stored under severe conditions of heavy load and high temperature.

In addition to the above, a fatty acid alkyl ester sulfonate metal salt powder with a narrow particle size distribution can be obtained by the present invention.

BRIEF DESCRIPTION OF THE DRAWINGS

FIG. 3-1 is a diagram showing the DSC peaks of a crystalline MES obtained by allowing the metastable solid MES with a water content of 1.9% to stand at 35° C. for 4 weeks; and FIG. 3-2 is a diagram showing the DSC peaks of a crystalline MES obtained by allowing the metastable solid MES with a water content of 3.3% to stand at 35° C. for 4 weeks.

FIG. 4 is a schematic diagram showing the baseline used as the reference for calculating the endotherm and explaining the way of splitting the peak.

FIG. 7 is a schematic diagram showing a cell used for evaluating the fluidity of granular detergent compositions.

DETAILED DESCRIPTION OF THE PRESENTLY PREFERRED EMBODIMENTS

Figure 1:
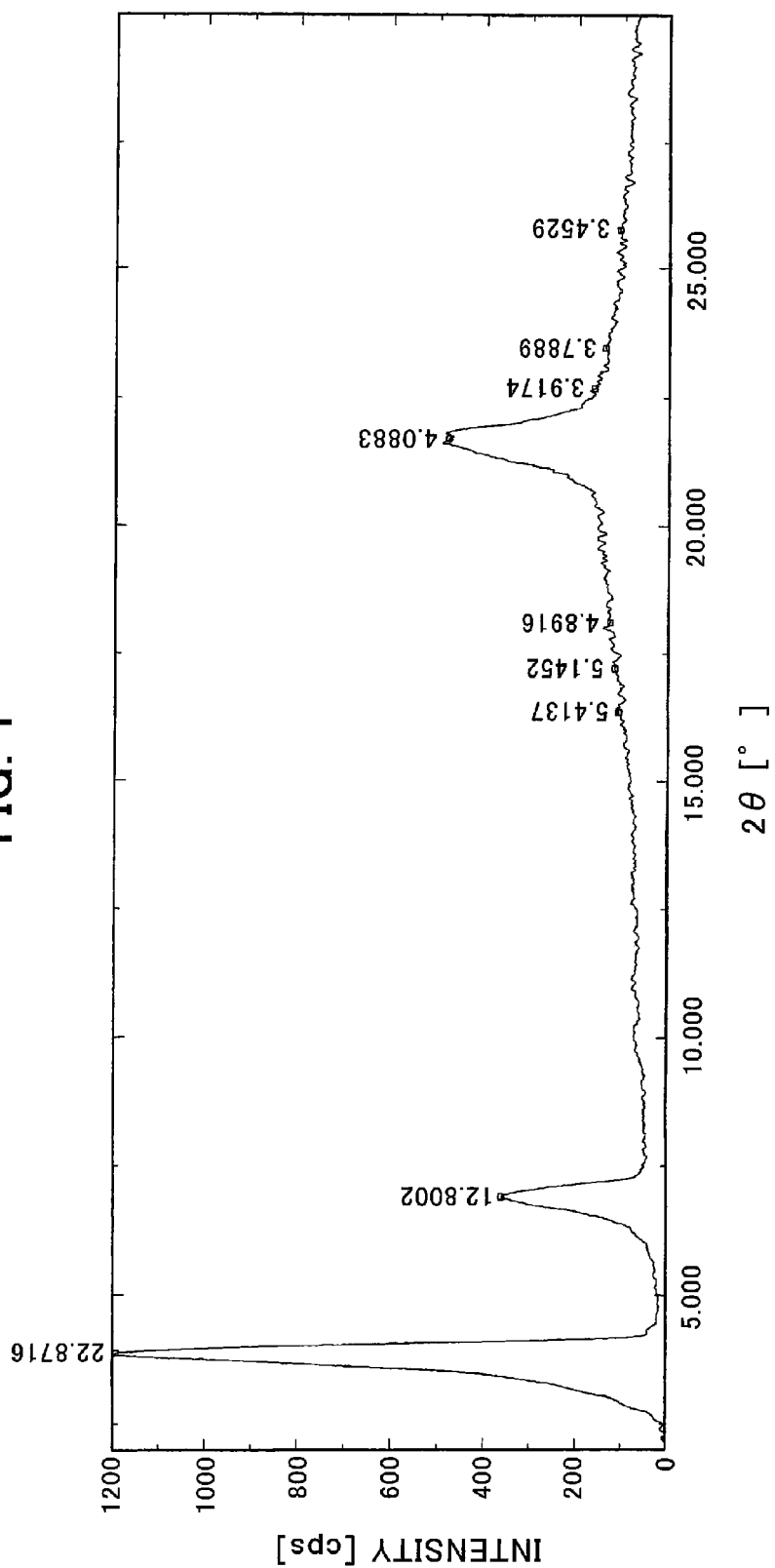
FIG. 1 is a diagram showing the X-ray diffraction peaks of a metastable solid MES.

Fatty acid alkyl ester sulfonate metal salt used as the raw material for the solid fatty acid alkyl ester sulfonate metal salt according to the invention is represented by the following formula (1):

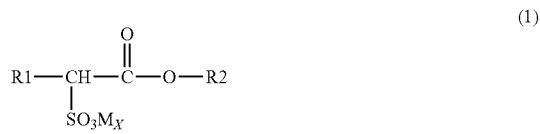

In the formula (1), $R^1$ is a straight-chain or branched alkyl or alkenyl group having 10 to 20 carbon atoms, preferably 10 to 18 carbon atoms, and more preferably 10 to 16 carbon atoms; $R^2$ is a straight-chain or branched alkyl group having 1 to 4 carbon atoms, preferably 1 to 2 carbon atoms; M is an alkali metal ion or alkaline earth metal ion, preferably an alkali metal ion, and more preferably sodium or potassium; and X is 1 when M is an alkali metal ion, and ½ when M is an alkaline earth metal ion.

In the invention, one kind of MES may be used alone, or two or more kinds may be used as a mixture. The latter is preferable. More preferably, the mixture may contain a compound represented by the above-mentioned formula (1) wherein $R^1$ represents a straight-chain or branched alkyl group or alkenyl group having 14 carbon atoms. Desirably, the mixture may contain the above-mentioned compound of formula (1) wherein $R^1$ represents a straight-chain or branched alkyl group or alkenyl group having 14 carbon atoms in an amount of 40 mass % or more, more preferably 60 mass % or more, and most preferably 80 mass % or more.

The fatty acid alkyl ester sulfonate metal salt mentioned above may be prepared by the conventional methods, or commercially available products may be used.

As the method for converting the fatty acid alkyl ester sulfonate metal salt into a crystal form (which method may also be referred to as aging method), for example, the steps (I) to (III) previously mentioned can be employed. Any other methods are available so long as the fatty acid alkyl ester sulfonate metal salt can be caused to crystallize.

The fatty acid alkyl ester sulfonate metal salt as the raw material is known to assume a variety of crystalline states. For example, 2-sulfopalmitic acid methyl ester sodium salt assumes stable crystalline states, such as anhydrous crystalline state, crystalline dihydrate, crystalline pentahydrate, and crystalline decahydrate. According to the report, the melting point of the anhydride is 112° C., and that of the above-mentioned dihydrate is 70° C. (M. Fujiwara, et. al., Langmuir, 13, 3345 (1997)).

The crystalline state of the MES as the raw material is not particularly limited. The MES forms a metastable solid when rapidly cooled after melted. More specifically, when the MES is melted at a temperature between 100° C. and 150° C. and then cooled to 0 to 40° C. three minutes or fewer after melting, the metastable solid MES can be obtained. The metastable solid is supposed to be a solid formed by supercooling the liquid crystal. The metastable solid MES is characterized by having a crystalline structure with three diffraction peaks respectively having peak tops between the lattice spacings of 20 and 30 Å, 10 and 15 Å, and 3 and 5 Å when determined by X-ray diffraction (FIG. 1).

It is difficult to form such a metastable solid from a pure MES, while the metastable solid state can be formed more easily when methyl sulfate metal salt and fatty acid sulfonate metal salt are blended. The methyl sulfate metal salt can decrease the viscosity of the MES in a paste form, thereby improving the handling properties. In addition, the metastable solid is considered to be an advantageous state in terms of the manufacturing process because the solid can be readily formed from the metastable solid by rapid cooling. In light of the above, the fatty acid alkyl ester sulfonate metal salt used as the raw material may desirably contain methyl sulfate metal salt and fatty acid sulfonate metal salt, which are by-products generated in the process of making a fatty acid alkyl ester into the sulfonate metal salt thereof. The methyl sulfate metal salt is represented by the following formula (2). The fatty acid sulfonate metal salt is represented by the following formula (3) or (4).

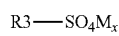
(2)

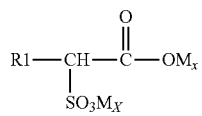
(3)

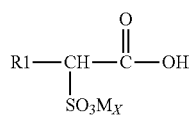
(4)

In the formula (2), $R^3$ is a straight-chain or branched alkyl group having 1 to 4 carbon atoms; and M and X are the same as those previously defined.

In the formulas (3) and (4), $R^1$, M and X are the same as those previously defined in formula (1).

In particular, the solid fatty acid alkyl ester sulfonate metal salt may be preferably produced from 60 to 98 mass % of a fatty acid alkyl ester sulfonate metal salt, 1 to 10 mass % of an alkyl sulfate metal salt, and 1 to 10 mass % of a fatty acid sulfonate metal salt. When the content of the MES is less than 60 mass %, the physical properties of the resultant solid may be more influenced by other materials than MES. When the content of the MES exceeds 98 mass %, the physical properties of the resultant solid may considerably change to worsen the handling properties during the production. When the content of the alkyl sulfate metal salt or the fatty acid sulfonate metal salt exceeds 10 mass %, the rate at which the metastable solid MES is converted into the crystal form according to the invention is significantly decreased. Particularly, a compound represented by formula (1) wherein $R^1$ is a straight-chain or branched alkyl or alkenyl group having 14 carbon atoms may be contained in an amount of 40 mass % or more, preferably 60 mass % or more, and more preferably 80 mass % or more of the total mass of the fatty acid alkyl ester sulfonate metal salt.

The above-mentioned step (I) for obtaining a solid fatty acid alkyl ester sulfonate metal salt according to the invention is a step of maintaining a metastable solid MES at 30° C. or more for at least 48 hours under pressure of 20,000 Pa or less.

When maintained at a temperature of less than 30° C., the metastable solid can convert into the crystal form of the invention, but extremely slowly. To maintain the metastable solid MES at 40° C. or less is desirable. When maintained at a temperature of more than 40° C., the metastable solid is found to slightly melt, and therefore, the metastable solid MES unfavorably tends to fuse to each other, thereby forming cakes during the storage. The temperature at which the metastable solid MES is maintained is not necessarily required to be constant as long as it is 30° C. or more. For example, intermittent heating and cooling is allowable. The way of setting the temperature is not particularly limited. For example, after the MES is placed into a container, the external environment of the container may be adjusted to the specified temperature. Alternatively, the container itself may be controlled to the specified temperature, or airflow of the specified temperature may be blown into the container. It is possible to use as the container, a silo, flexible container bag, drum, craft paper bag, polyethylene bag or the like.

Caking may occur when the metastable MES is maintained at a pressure exceeding 20,000 Pa. Practically, while the MES is filled into the container for storage, due to the weight of MES itself, pressure will inevitably be exerted especially on the bottom part of the container. The pressure herein used means a pressure to be exerted on the bottom surface, which is defined by the following formula: pressure (Pa)=the mass (kg) packed in a container×acceleration of gravity g (m/s$^2$)/ the area of base (m$^2$) of the container. To maintain the metastable solid MES under 12,000 Pa or less is desirable. It is further preferable to maintain the metastable solid IVIES under 500 to 8,000 Pa.

When the maintaining time is less than 48 hours, the conversion from the metastable state to the crystal form of the present invention may become insufficient. The maintaining time is also 6 weeks at the longest, preferably 72 hours or more.

While the MES is maintained under the above-mentioned conditions, the container holding the MES therein may be tightly sealed or left open. When the container is left open, the contact with damp air should be avoided in consideration of the effects of moisture absorption.

In particular, it is preferable to maintain the metastable solid MES at 30 to 35° C. and 3,000 to 7,000 Pa for 200 to 400 hours.

The melting point of the obtainable solid fatty acid alkyl ester sulfonate metal salt is as high as 50° C. or more, so that the solid material is resistant to melting even when stored at high temperatures.

The above-mentioned step (II) for obtaining a solid fatty acid alkyl ester sulfonate metal salt according to the invention is a step of melting the metastable solid fatty acid alkyl ester sulfonate metal salt and maintaining the obtained melt for 5 minutes or more at a temperature from the melting point of the metastable solid fatty acid alkyl ester sulfonate metal salt to the melting point of the solid fatty acid alkyl ester sulfonate metal salt.

The above-mentioned temperature can be decided from the melting points of the metastable solid and the crystal form of the MES. The melting points of the metastable solid and the crystal form may be determined in advance using a differential scanning calorimeter (DSC).

For example, when the fatty acid alkyl ester sulfonate metal salt represented by the above-mentioned formula (1) is used as the raw material, the melt is preferably maintained at a temperature of 40° C. or more and less than 90° C., more preferably 50° C. or more and less than 80° C. When the temperature is not within the above-mentioned range, it may become difficult to form a crystal form in a short time. In addition, when the maintaining time is less than 5 minutes, the solid material may not reach such a stable state as specified by the DSC.

In particular, the melt may be preferably maintained at 55 to 75° C. for 10 to 500 minutes.

The above-mentioned step (III) for obtaining a solid fatty acid alkyl ester sulfonate metal salt according to the invention is a step of melting the metastable solid fatty acid alkyl ester sulfonate metal salt and applying a shearing force to the obtained melt at a shear rate of 100 (1/s) or more at a temperature from the melting point of the metastable solid fatty acid alkyl ester sulfonate metal salt to 80° C.

The step (II) previously mentioned makes it possible to obtain a solid MES by allowing the MES melt to stand at a predetermined temperature for a given time; while the step (III) can accelerate the conversion into the crystal form by applying a shearing force to the melt instead of leaving the melt standing for a given time.

The means for applying a shearing force is not particularly limited, and for example, a variety of kneaders and extrusion granulators may be used. To be more specific, the commercially available apparatus such as KRC kneader made by Kurimoto, Ltd., Milling Prodder made by Mazzoni S.p.a and the like can be used.

The shear rate is defined by dividing the impeller tip speed by clearance. In the step (III), the shear rate is 100 (1/s) or more, preferably 150 (1/s) or more. When the shear rate is less than 100 (1/s), the agitation performance may be insufficient to make the solid material into such a stable state as specified by the DSC.

Preferably, the shearing operation may be carried out for five seconds or more and less than five minutes. With the shearing time of less than five seconds, it is hard to obtain a stable solid material. To carry out the shearing operation for more than five minutes, extremely large-scale apparatus will be needed.

Particularly, the shearing force may be applied at a shear rate of 200 to 5,000 (1/s) at 55 to 75° C.

Figure 2:
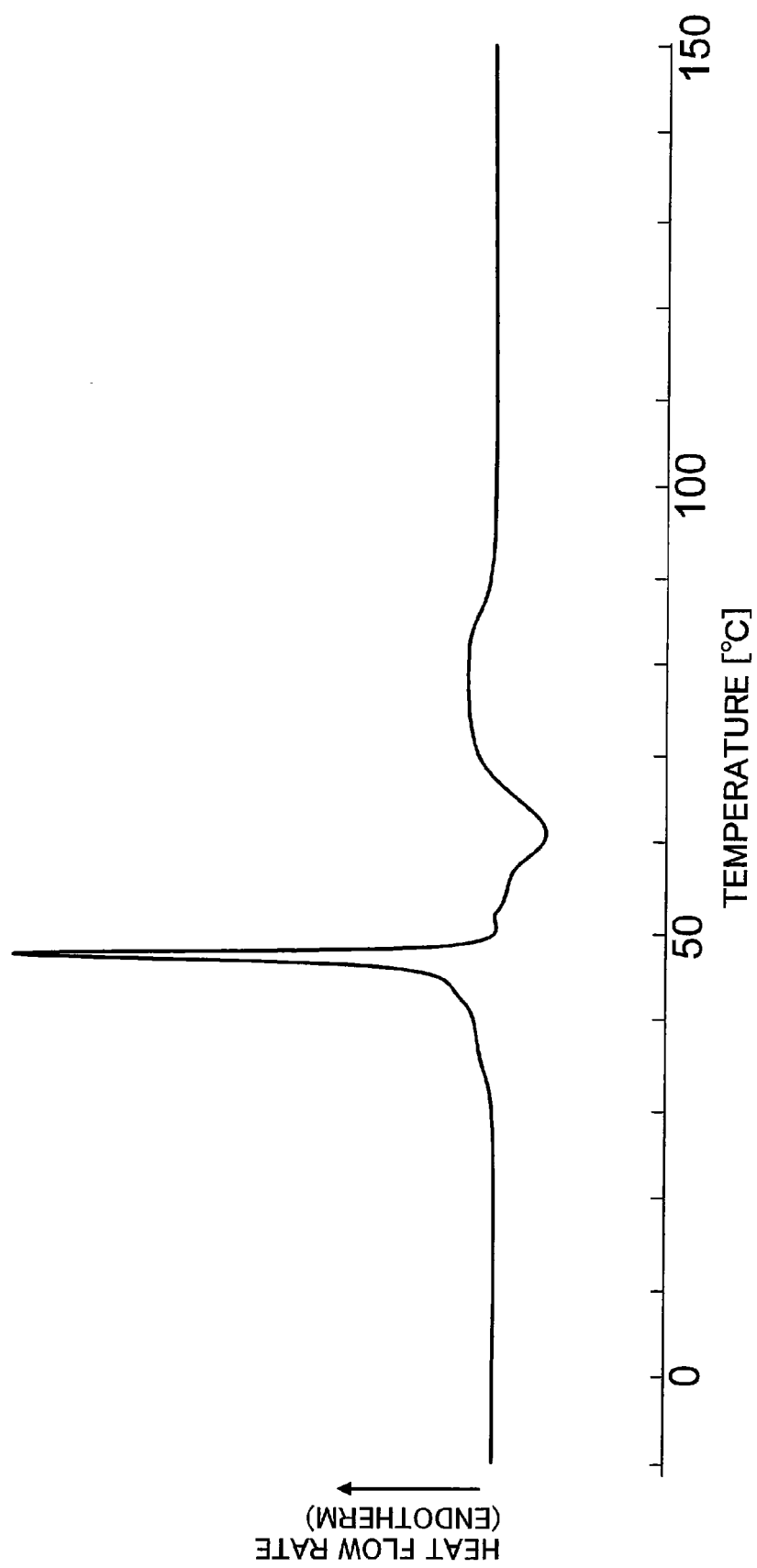
FIG. 2 is a diagram showing the DSC peaks of a metastable solid MES.
Figures 2, 3:
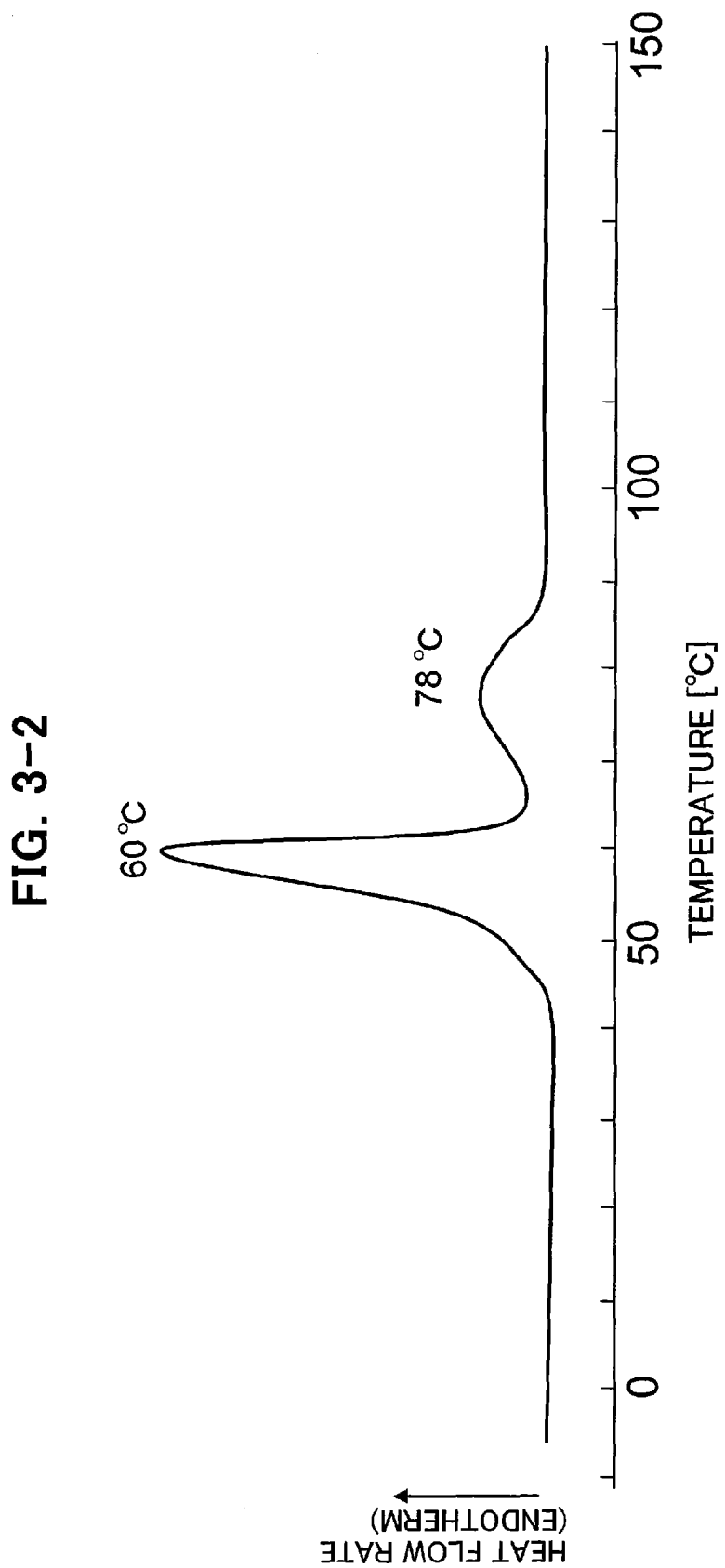
FIG. 3 shows the DSC peaks of a crystalline MES according to the invention.

The DSC peaks of the crystalline MES according to the invention are different from those of the metastable solid MES, which will be explained by referring to the MES prepared from a mixture of two compounds of formula (1) wherein $R^1$ has respectively 14 carbon atoms and 16 carbon atoms. The endothermic peak appears between about 35° C. and about 55° C. according to the DSC of the metastable solid MES, which shows the melting peak having a peak top between about 40° C. and about 50° C. (FIG. 2). In contrast to this, the endothermic peak is observed over about 50° C. in the DSC of the crystalline MES (FIG. 3). When FIG. 3 is compared with FIG. 2, the MES in crystalline form has shorter peaks around 40 to 50° C. as shown in FIG. 3 and is said to be more stable over the higher temperature range, in contrast to the metastable solid MES as shown in FIG. 2. Further, in the crystalline MES according to the invention, a plurality of peaks appearing between about 50° C. and about 70° C. and between about 70° C. and about 90° C. are observed as the endothermic peaks, and the absolute value of the latter endothermic peak is higher when the water content is lower (FIGS. 3-1 and FIGS. 3-2).

In the solid fatty acid alkyl ester sulfonate metal salt of the invention, the endothermic peak area A between 50° C. and 130° C., determined by a differential scanning calorimeter is 50% or more, preferably 70% or more, relative to the whole endothermic peak area B between 0° C. and 130° C. The whole endothermic peak area B is the shaded area+the endothermic peak area A marked with diagonal lines. When the area A is less than 50% of the whole endothermic peak area B, the caking will often take place.

The ratio of A to B as specified by the invention is determined by placing a sample for analysis into an aluminum pan or stainless steel pan and measuring the endotherm and exotherm at a predetermined heating rate using a differential scanning calorimeter. Under certain circumstances, exothermic peaks may be observed at a temperature of less than 100° C. In this case, the value A is obtained by subtracting the exotherm from the endotherm over 50° C. Similarly, for the value B, a total endotherm is obtained by subtracting the absolute value of exotherm of the exothermic peaks from the endotherm of the endothermic peaks.

The endotherm is calculated with reference to a baseline, which is defined by the straight line obtained by joining straight-line segments before and after the endothermic peak.

By referring to a diagram shown in FIG. 4, those skilled in the art could easily understand how to determine the baseline and how to split the peak.

The melting point is defined by a peak top value. For example, the melting point of the metastable solid is defined as a peak top of the peak appearing around temperatures of less than 50° C., as shown in FIG. 2. The melting point of the crystalline MES solid is defined as a temperature corresponding to a peak top of the peak appearing in a higher temperature region, that is, between 50° C. and 130° C. Specifically, the peak in FIGS. 3-1 and the peak of the higher temperature region in FIGS. 3-2 are respectively 88° C. and 78° C. The melting point of the crystalline MES solid varies depending on the water content and other components contained in the MES. With the conversion from the metastable solid to the crystal form of MES, the peak in the higher temperature region is shifted. Also, to determine the melting point of the crystalline MES, the same measurement by the DSC is carried out using a cell holding therein an appropriate sample. The melting point of the crystalline MES is regarded as the temperature corresponding to the peak top of a peak appearing at the highest temperature among the peaks of which intensities are 10% or more relative to that of the maximum peak. If the melting point is not definite, the measurement may be conducted after the sample is stored at 45° C. for one week. This process can clearly define the melting point.

As for the differential scanning calorimeter, any commercially available differential scanning calorimeters, including power-compensation type and heat-flux type can be used. For example, the commercially available calorimeters such as Diamond DSC (Perkin Elmer Inc.), EXSTAR 6000 (Seiko Instruments Inc.) and the like can be used. As the sample pan, an aluminum or stainless steel pan is used. The heating rate is preferably 1 to 2° C./min. When the heating rate is slower than the above-mentioned rate, the noise will increase. When the heating rate becomes more rapid, detection of minute peaks may become impossible.

Figure 5:
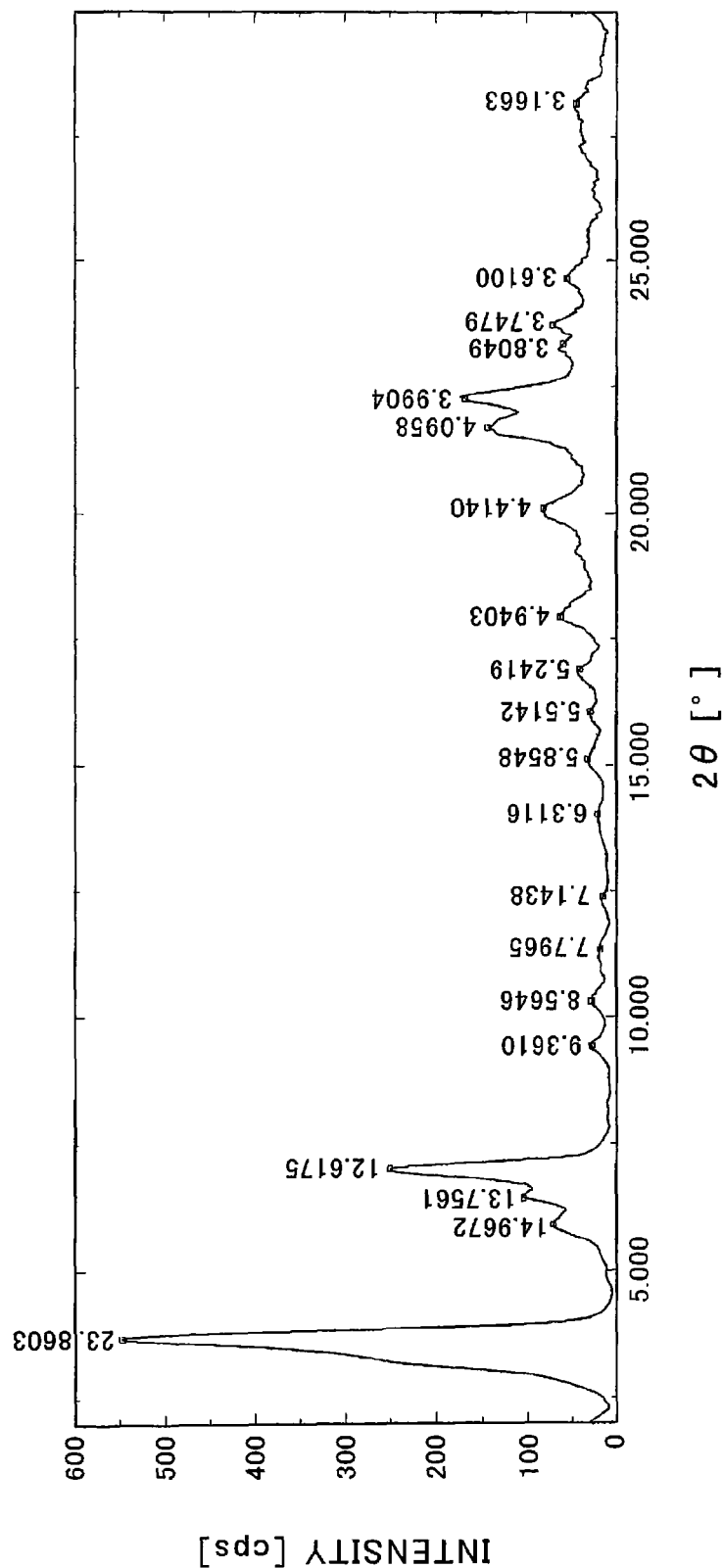
FIG. 5 is a diagram showing X-ray diffraction peaks of a crystalline MES according to the invention.

When the crystalline MES according to the invention is subjected to X-ray diffraction, many reflections probably resulting from the crystal lattice are detected (FIG. 5). In light of this, the crystalline MES according to the invention is considered to form a molecular crystal with a general Bravais lattice. It will be easy to distinguish whether the MES assumes the crystal form specified by the invention or the metastable solid state because the X-ray diffraction (FIG. 1) of the metastable solid MES showing three broad reflection peaks is apparently different from that of the crystalline MES.

Figures 1, 6:
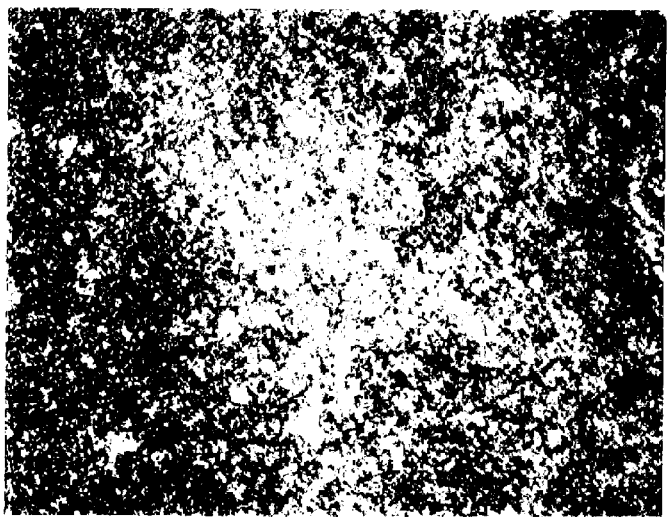
FIG. 6 is a series of microscope photographs showing a crystalline MES according to the invention. The height of the microscope photograph corresponds to 750 μm and the width thereof corresponds to 1000 μm.
Figures 2, 6:
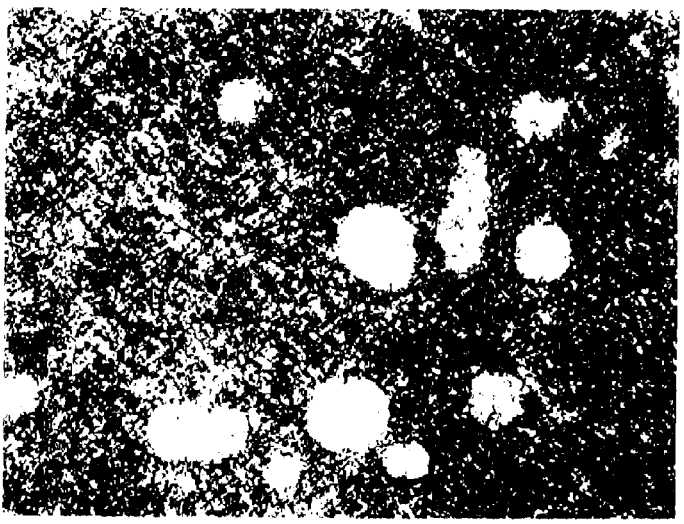
Figures 3, 6:

It is also possible to observe the crystal form of the present invention using a microscope, although it depends on the crystal growing process. When the MES in a metastable state is melted, followed by rapid cooling, a solid phase with a homogeneous polarization is observed as shown in FIGS. 6-1. When the MES in a metastable state is melted and then allowed to stand at 60° C., the crystals are growing and needle crystals are then observed (FIGS. 6-2), and at last the needle crystals become predominant (FIGS. 6-3). The crystals may grow concentrically, with the seed crystal as the central point as shown in this figure, or the needle crystals may homogeneously grow.

The results of the DSC, X-ray diffraction and microscopic observation can demonstrate that the crystalline MES of the present invention is distinctly different from the known metastable MES in the physicochemical condition. It is also said that the presence of the crystal form can be recognized by the DSC and the X-ray diffraction.

The crystalline MES according to the invention is stable. When the crystalline MES of the present invention exists together with the MES not in the crystalline state, the melting portion can be reduced under the circumstances of high temperature, for example, as high as 40° C. or more if only the crystalline MES according to the present invention makes up 50% or more. As a result, the adhesion ascribable to the metastable solid MES can be reduced, thereby controlling the caking properties.

The crystalline MES according to the invention may preferably have a water content of 10% or less, more preferably 5% or less. When the water content exceeds 10%, the preservation stability of the crystalline MES according to the invention will tend to deteriorate. This will increase the adhesion properties at low temperatures, and therefore the degree of improvement in storage properties and transportability may drastically decrease. The lower limit is preferably 0.5% or more.

The crystalline MES according to the invention may be used in various forms, preferably in the form of flakes or particles.

When the fatty acid alkyl ester sulfonate metal salt-containing product is melted and then cooled, it will assume a solid state. In the course of cooling, the melt is formed into plate-shaped solid using a drum flaker, belt cooler or the like, and then crushed, thereby obtaining flakes. Examples of the flaker include Drum Flaker made by Katsuragi Industry. Co., Ltd., and Drum Flaker FL made by Mitsubishi Materials Corporation. Examples of the belt cooler include Double Belt Cooler and NR type Double Belt Cooler made by Nippon Belting Co., Ltd., and a double belt cooling system made by Sandvik Materials Technology. As the crusher, for example, Flake Crusher FC made by Hosokawa Micron Corporation or the like can be used.

The particles of crystalline MES according to the invention include, for example, pellets, noodles, ground products thereof, powders and the like. Other forms are available.

The MES powder can be prepared using a pulverizer. The pulverizer includes, for example a hammer mill, a pin mill and the like. As the hammer mill, Feather Mill FS made by Hosokawa Micron Corporation and Fitzmill made by Fitzpatrick Company can be used.

The pellets and noodles can be produced in such a manner that the melted fatty acid alkyl ester sulfonate metal salt-containing product or flakes are charged into an extrusion granulator or kneader and then passed through a die having an appropriate diameter, or the like. The obtained product is cooled, and then crushed into a desired size using the above-mentioned crusher or the like. Examples of the extrusion granulator include Pelleter Double and Twin Dome Granulator, made by Fuji Paudal Co., Ltd., and Gear Pelletizer and Extrud-O-Mix, made by Hosokawa Micron Corporation.

When the crystalline MES according to the invention is in the form of flakes or particles, the mean particle diameter, which will be defined later, may be at least 3 mm, more preferably 5 mm or more and 100 mm or less. When the mean particle diameter is less than 3 mm, the number of contact points and the contact area increase, so that the particles cannot withstand the increased adhesion between the particle surfaces to readily tend to induce caking with the increase of temperature.

In the case where the mean particle diameter is supposed to be 3 mm or more, the mean particle diameter is determined by the following method. The axis having a maximum length of a flake or particle is supposed to be X; the axis of a cross section having a maximum length, perpendicular to the axis X is supposed to be Y; the axis perpendicular to the two axes X and Y is supposed to be Z. The diameter obtained by averaging the total of the maximum length of X, the maximum length of Y and the length of Z axis is regarded as a characteristic diameter of one particle. The characteristic diameters of 50 or more flakes or particles are measured and the weight average value is obtained.

With respect to the flakes or particles including those with a particle diameter of less than 3 mm, the flakes or particles are subjected to dry-sieving according to JIS Z8815 and the percentage of cumulative undersize distribution is plotted on the Rosin-Rammler's chart. The mean particle diameter is regarded as that indicating the percentage of 50%, which is added to the above-mentioned percentage as the weight average value.

The solid fatty acid alkyl ester sulfonate metal salt according to the invention may be further finely pulverized to obtain a fatty acid alkyl ester sulfonate salt metal powder (hereinafter also referred to as MES powder), which may be used in the granular detergent compositions for the textile goods and granular detergent compositions for the dishes. The ingredients contained in those granular detergent compositions include: an anionic surfactant such as MES, straight-chain alkylbenzene sulfate metal salt, α-olefin sulfonic acid metal salt, alkylsulfate metal salt, metal salt of soap or the like; a nonionic surfactant such as alkyleneoxide adduct of higher alcohol; a builder, for example, an inorganic builder such as zeolite, sodium sulfate, sodium sulfite or the like; an alkali chemical, for example, sodium carbonate, potassium carbonate or the like; a fluorescent agent; a bleaching agent; a bleaching activator; an enzyme; a perfume; a softening agent such as bentonite, cationic cellulose, powdered cellulose or the like.

As compared with the case where the finely ground product of the metastable solid MES is used, the ground product (MES powder) prepared from the flakes or particles of the crystalline MES according to the invention can keep higher fluidity as a whole even when exposed to high temperatures.

When contained in the general-purpose granular detergent compositions for the clothes and granular detergent compositions for the dishes, the content of MES is preferably 1 mass % or more and 50 mass % or less, and more preferably 5 mass % or more and 40 mass % or less. When the MES content is 1 mass % or more and 50 mass % or less, it is possible to obtain a granular detergent composition with high fluidity.

The caking tendency of the MES powders can be further reduced by covering the MES powders with a coating.

The coating agent includes inorganic powders and powders of organic acid salts and the like, which may be water-soluble or not. One kind of coating agent may be used alone or two or more kinds may be appropriately used in combination. Examples of the inorganic powders are aluminosilicate such as zeolite A, sodium carbonate, alkaline earth metal salt carbonates such as calcium carbonate and magnesium carbonate, amorphous silica, white carbon (silica), silicates such as sodium silicate, calcium silicate, magnesium silicate and the like, clay minerals such as talc, bentonite and the like, silicon dioxide, titanium dioxide, finely-divided particles of sodium carbonate, sodium sulfate, potassium sulfate, sodium tripolyphosphate and the like. Of the above coating agents aluminosilicate, sodium carbonate and sodium sulfate are preferable. Examples of the organic acid salts include metallic soap such as stearates, sodium acetate, sodium citrate and the like. In particular, stearates are preferred.

The finely ground product of metastable solid MES tends to cake at high temperatures even though the finely ground product is covered with the coating agent as mentioned above.

The amount of the coating agent is preferably 1 to 30 mass %, more preferably 1 to 20 mass %, and most preferably 5 to 10 mass %, based on the mass of the MES powder.

When the amount of the coating agent is less than 1 mass %, the additional improvement effect on the caking properties cannot be expected. When the amount of coating agent exceeds 30 mass %, the degree of freedom in formulation of other ingredients may be lowered when the coated MES powder is used in the general-purpose granular detergent compositions for the clothes and granular detergent compositions for the dishes.

As the coating method, the MES powder may be mixed with the coating agent, or the coating agent may be added to the flakes or particles of the crystalline MES, followed by grinding.

The mean particle diameter of the coated MES powder may be preferably 300 μm or more and 3 mm or less. When the mean particle diameter is 300 μm or more, the caking properties can be further reduced. When the mean particle diameter of coated MES powder is 3 mm or more, the problem of classification or the like may be produced in the case where the coated MES powder is blended into the general-purpose granular detergent compositions for textile goods and the dishes because the particle size of the coated MES powder becomes too large among all the particles constituting the composition. The mean particle diameter is a value obtained by the method of "Determination of mean particle diameter of powders of less than 3 mm" in the Examples to be described later.

When the crystalline MES solid according to the invention is subjected to pulverizing, the pulverizing operation can be carried out at high temperatures without adhesion to the pulverizer. Therefore, it becomes possible to obtain MES powder with a sharp particle size distribution.

The MES powder can be prepared using a pulverizer. The same pulverizers as used in the preparation of the crystalline MES are usable.

In the course of pulverizing, the internal temperature of the pulverizer is not particularly limited, but preferably 30° C. or more and 50° C. or less, more preferably 30° C. or more and 40° C. or less, and most preferably 33° C. or more and 38° C. or less. When the internal temperature is less than 30° C., the particle size distribution of the obtainable powder becomes broad and the amount of fine particles may increase. When the internal temperature exceeds 50° C., the powders may adhere to the pulverizer because of the increased adhesion of the powders.

Although the temperature of the inside of the pulverizer is not particularly limited, the temperature may be controlled by adjusting the temperature of airflow in the case where the airflow is blown into the pulverizer in the course of pulverizing. Alternatively, even if the airflow is not blown into the pulverizer, the internal temperature of the pulverizer may be controlled by adjusting the temperature of flakes or externally warming of the pluveraizer. The inside of the pulverizer herein used means the inner part of a container which encloses and holds a portion where the blade, hammer or the like is driven to actually pulverize the flakes or the like.

In particular, pulverizing may be carried out, with a screen been provided. The screen with a pore diameter of 2 mm is used when the increase of coarse particles is expected; and the screen with a pore diameter of 3 mm is used when the increase of fine particles is expected. As a matter of course, the obtained particle size becomes larger by using the screen with larger pores; and smaller by using the screen with smaller pores.

The inventors have found that the amount of coarse powders can especially be reduced by increasing the number of revolutions (i.e., peripheral speed) in the pulverizing operation. It is preferable to carry out the pulverizing operation at 200 to 8000 rpm, more preferably 600 to 5000 rpm. The particle size tends to decrease with the increase of the number of revolutions, while the particle size tends to increase with the decrease of the number of revolutions. The peripheral speed (i.e., the peripheral speed of rotary blade tips) may be preferably in the range of 20 to 70 m/s, more preferably 30 to 60 m/s, and most preferably 35 to 55 m/s.

The pulverizing time is generally from five seconds to five minutes.

The multiple-stage pulverizer can be used where pulverizing units are arranged in series or in parallel.

The particle size distribution of the MES powder obtainable by the production method of the invention may preferably be 50 mass % or less (1000 μm on) and 10 mass % or less (149 μm pass), more preferably, 8 mass % or less (1000 μm on) and 8 mass % or less (149 μm pass). The above-mentioned particle size distribution is advantageous in terms of the solubility. The particle size distribution can be determined in such a manner as described in the Examples to be given later.

The MES powder (not coated) obtainable by the production method of the invention may preferably have a mean particle diameter of 300 to 3,000 μm, more preferably 400 to 600 μm. The mean particle diameter within the above range is advantageous in terms of the solubility. The mean particle diameter can be determined in such a manner as described in the Examples to be given later.

The MES powder obtainable by the production method of the invention may preferably have a bulk density of 0.55 to 0.75 kg/L, more preferably 0.60 to 0.70 kg/L.

The bulk density within the above-mentioned range is preferred because of the advantages of space-saving and good solubility. The bulk density can be determined in accordance with the JIS K 3362.

The inorganic powder may also be pulverized together in the course of the production of the MES powder. Any inorganic powder that is generally used for the production of granular detergent compositions can be employed with no restrictions. The inorganic powder with a mean particle diameter of 0.1 to 100 μm, preferably 0.5 to 50 μm, and more preferably 0.5 to 30 μm may be used. When the mean particle diameter of the inorganic powder is less than 0.1 μm, the dusting properties may worsen in some cases. With the mean particle diameter of more than 100 μm, the mixed powder may become heterogeneous by size separation during the storage time. The mean particle diameter of the inorganic powder can be determined using a laser diffraction/scattering type particle size analyzer, for example, Partica LA-950V2, made by Horiba, Ltd., LDSA-1400A made by Tohnichi Computer Applications Co., Ltd., or the like.

The inorganic powder may be mixed in an amount of 30 mass % or less, preferably 1 to 20 mass %, and more preferably 5 to 10 mass %, based on the total mass of the finished product, in consideration of the effect of upgrading the powder properties of MES. The inorganic powder, which may not be necessarily mixed with the MES powder, can contribute to prevention of the caking of powder during the long-term storage more effectively. When the amount of inorganic powder exceeds 30 mass %, there occurs a problem in fluidity of the mixture powder.

The inorganic powder may be fed into the pulverizer before the flakes or pellets are subjected to pulverizing, or during or after the pulverization of the flakes or pellets. To mix the inorganic powder with the flakes or pellets or ground powders, any apparatus designed for dry blending can be used with no limitation.

Specific examples of the apparatus are a horizontal drum-shaped blender, V-shaped mixer, and agitating granulator, which are considered as illustrative and not restrictive.

EXAMPLES

Preparation of Examples 1-10 and 12-17

As the raw material for producing a solid fatty acid alkyl ester sulfonate metal salt, fatty acid alkyl ester sulfonate metal salt in the form of flakes (hereinafter also referred to as "MES flakes") was prepared by the method shown below.

Methyl palmitate ("PASTELL M-16", made by Lion Corporation) and methyl stearate ("PASTELL M-180" made by Lion Corporation) were used as the raw materials. The methyl palmitate and the methyl stearate were mixed at a ratio (by mass) as shown in Table 1 (in the column of carbon chain length ratio).

In a 1-kL reaction vessel equipped with a stirrer, 330 kg of the above-mentioned fatty acid methyl ester mixture was introduced, and then anhydrous sodium sulfate was added as the coloring inhibitor in an amount of 5 mass % with respect to the above-mentioned fatty acid methyl ester mixture, with stirring. While keeping on stirring, 110 kg (equivalent to 1.1 moles to one mole of methyl ester mixture as the raw material) of $SO_3$ gas (sulfonating gas) which was diluted to 4 vol % with nitrogen gas was blown into the mixture with bubbling, at a constant rate over a period of 3 hours at the reaction temperature of 80° C. The reaction mixture was then subjected to aging at 80° C. for 30 minutes.

After the reaction mixture was transferred to an esterification reaction vessel, 14 kg of methanol was charged into the vessel, thereby causing an esterification reaction at 80° C. The reaction mixture was then subjected to aging at 80° C. for 30 minutes.

Then, the esterified product extracted from the reaction vessel was continuously neutralized by the addition of a sodium hydroxide aqueous solution equivalent to the esterified product using a line mixer.

Subsequently, the above-mentioned neutralized product was fed into a bleaching agent mixing line, where a 35% hydrogen peroxide solution was added in a substantial amount of 1 to 2% with respect to the active ingredient (AI, i.e., α-sulfo fatty acid alkyl ester metal salt). The neutralized product was mixed with the bleaching agent at 80° C. to carry out the bleaching step, so that a fatty acid alkyl ester sulfonate metal salt-containing paste was obtained.

The fatty acid alkyl ester sulfonate metal salt-containing paste thus obtained was introduced into a vacuum thin-film evaporator (with a heat transfer surface of 4 $m^2$, made by Ballestra) at a feed rate of 200 kg/hr and concentrated at an inner wall heating temperature of 100 to 160° C. and at a degree of vacuum of 0.01 to 0.03 MPa, thereby obtaining a melt product of 100 to 130° C. After cooled, the fatty acid methyl ester sulfonate sodium salt (MES) contained in the melt was titrated in accordance with the methylene blue (MB) back titration described in the JIS K3362, and the contents of the di-sodium salt (DiNa), sodium methylsulfate ($MeSO_4Na$) and sodium sulfate ($Na_2SO_4$) were determined by liquid chromatography. The conditions of measurement were as follows:

(DiNa)
Column: Nucleosil 100-5SB (made by GL Sciences Inc.)
Eluent: 0.7% solution of sodium perchlorate in a mixture of water and methanol (⅔ vol/vol)
($MeSO_4Na$) and ($Na_2SO_4$)
Column: TSKgel Super IC-Anion (made by TOSOH Corporation)
Eluent: aqueous solution of 1.7 mM sodium bicarbonate and 1.8 mM sodium carbonate The water content was measured using a Karl Fischer moisture titrator ("MKC-210" made by Kyoto Electronics Manufacturing Co., Ltd.) after the MES melt was solidified by cooling and crushed in a mortar.

The results are shown in Table 1.

TABLE 1

| Preparation Examples | MES carbon chain length ratio C16/18 | MES | DiNa | MeSO4Na | Na2SO4 | Water content | Mp of Metastable Solid (° C.) |
|---|---|---|---|---|---|---|---|
| 1 | 99/1 | 84 | 4.2 | 6.2 | 2.6 | 2.1 | 48 |
| 2 | 90/10 | 84.6 | 3.7 | 6.7 | 2.7 | 1.5 | 46 |
| 3 | 90/10 | 82.5 | 4.6 | 7.0 | 2.9 | 1.9 | 46 |
| 4 | 90/10 | 84.2 | 3.4 | 6.8 | 2.9 | 2.0 | 46 |
| 5 | 90/10 | 83.1 | 3.8 | 6.8 | 3.0 | 3.0 | 45 |
| 6 | 80/20 | 84.8 | 3.8 | 6.8 | 2.9 | 2.2 | 46 |
| 7 | 60/40 | 83.7 | 4.1 | 6.7 | 2.8 | 2.2 | 46 |
| 8 | 45/55 | 84.2 | 3.7 | 4.4 | 4.6 | 2.2 | 47 |
| 9 | 99/1 | 84.2 | 3.9 | 5.8 | 2.5 | 3.1 | 49 |
| 10 | 99/1 | 82.5 | 3.8 | 5.7 | 2.4 | 5.1 | 49 |
| 11 | 100/0 | 86.0 | 4.0 | 4.2 | 4.1 | 1.7 | 49 |
| 12 | 80/20 | 84.0 | 4.2 | 5.7 | 2.5 | 3.2 | 48 |
| 13 | 60/40 | 83.1 | 5.3 | 5.2 | 3.1 | 3.0 | 46 |
| 14 | 45/55 | 84.1 | 5.5 | 5.1 | 3.0 | 2.0 | 45 |
| 15 | 45/55 | 82.4 | 5.7 | 4.9 | 3.0 | 3.0 | 45 |
| 16 | 80/20 | 82.9 | 4.0 | 6.6 | 2.7 | 3.3 | 46 |
| 17 | 99/1 | 81.5 | 4.6 | 6.4 | 2.7 | 3.8 | 47 |

Then, the above-mentioned melt was cooled to 20 to 30° C. over a period of 0.5 minutes using a belt cooler (made by Nippon Belting Co., Ltd.), thereby obtaining a metastable solid MES. The melting point of the metastable solid was determined by the DSC. The results are shown in Table 1. After that, the metastable solid was crushed using a crusher (made by Nippon Belting Co., Ltd.), to obtain MES flakes.

Preparation of Example 11

In a separable round flask, methyl palmitate ("PASTELL M-16", made by Lion Corporation) as the raw material was reacted with nitrogen-diluted $SO_3$ gas for sulfonation at a reaction molar ratio ($SO_3$/saturated fatty acid methyl ester) of 1.2 and at a reaction temperature of 80° C., so that a sulfonated product was obtained. The sulfonated product thus obtained was subjected to aging at 80 to 85° C. for 30 minutes to complete the sulfonation, so that 2-sulfo palmitic acid methyl ester was obtained. Then, 20 parts by mass of methanol were added to 100 parts by mass of the 2-sulfo palmitic acid methyl ester, and then 5.7 parts by mass of a 35% hydrogen peroxide solution were added. The resultant mixture was maintained at 80 to 85° C. for 30 minutes for bleaching. To the bleached acid thus obtained, an aqueous solution of sodium hydroxide at a predetermined concentration was added, followed by vigorous stirring by means of JET AJITER (Type: SJ), made by Shimazaki Mixing Equipment Co., Ltd., to adjust the mixture to pH7. The MES salt composition thus obtained was caused to evaporate on an evaporating dish, thereby eliminating methanol and concentrating the composition. The MES concentrate was thus obtained. The resultant MES concentrate was stirred in a bench kneader (PNV-1, made by IRIE SHOKAI Co., Ltd.), with hot water of 95° C. being allowed to pass through the jacket, until the water content of the concentrate reached 2.6%. The obtained melt was sandwiched between stainless steel plates and cooled. Subsequently, the cooled product was crushed with the hands to obtain the flakes.

The contents of the individual components present after the melt was cooled were determined by the same methods as previously described in Preparation Examples 1 to 10 and 12 to 17.

With respect to the melting points given in Table 1 showing Preparation Examples 1 to 17, the melting points of the flakes prepared by the above-mentioned methods were determined by the DSC as in the description of "Determination of melting point, endotherm and exotherm by DSC".

Examples 1-10

According to the simple examination to be described later, the MES flakes prepared in Preparation Example 1, 2, 3, 5, 6, 10, 13 or 15 were placed into a cell and allowed to stand at the temperature and the pressure as indicated in Table 2 for the period of time also as indicated in Table 2.

The DSC and the caking properties of the obtained solid fatty acid alkyl ester sulfonate metal salt were determined. The caking properties were determined by the simple examination. The results are shown in Table 2.

Comparative Example 1

The MES flakes obtained in Preparation Example 4 were not subjected to aging (i.e., crystallization), and the DSC and the caking properties of the MES flakes were determined by the simple examination to be described later. The results are shown in Table 2.

Comparative Example 2

According to the method of simple examination to be described later, the MES flakes prepared in Preparation Example 3 were placed into a cell and allowed to stand at the temperature and the pressure as indicated in Table 2 for the period of time also as indicated in Table 2.

The DSC and the caking properties of the obtained IVIES flakes were determined. The caking properties were determined by the simple examination. The results are shown in Table 2.

TABLE 2

|  | Comparative Example 1 | Comparative Example 2 | Example 1 | Example 2 | Example 3 | Example 4 |
|---|---|---|---|---|---|---|
| MES carbon chain length ratio C16/18 (mass ratio) | 90/10 | 90/10 | 90/10 | 99/1 | 80/20 | 90/10 |
| Water content (mass %) | 2.0 | 1.9 | 1.9 | 2.1 | 2.2 | 1.5 |
| Preparation Example No. of MES flakes | 4 | 3 | 3 | 1 | 6 | 2 |
| Mean particle diameter (mm) | 9.2 | 9.3 | 9.3 | 8.9 | 9.5 | 9.1 |
| Temperature in aging step (° C.) | — | 25 | 30 | 30 | 30 | 30 |
| Pressure in aging step (Pa) | 5000 | 5000 | 5000 | 5000 | 5000 | 5000 |
| Aging period of time (days) | 0 | 14 | 14 | 14 | 28 | 14 |
| Ratio of endothermic peak area between 50° C. and 130° C. by DSC (%) | 0 | 31 | 73 | 91 | 87 | 62 |
| Determination method of caking properties | Simple* | Simple* | Simple* | Simple* | Simple* | Simple* |
| Number of drops | 100 or more | 15 | 1 | 0 | 1 | 0 |
| Rating of caking properties | x | x | ∘∘ | ∘∘ | ∘∘ | ∘∘ |

|  | Example 5 | Example 6 | Example 7 | Example 8 | Example 9 | Example 10 |
|---|---|---|---|---|---|---|
| MES carbon chain length ratio C16/18 (mass ratio) | 90/10 | 99/1 | 90/10 | 60/40 | 45/55 | 99/1 |
| Water content (mass %) | 3.0 | 2.1 | 1.9 | 3.0 | 3.0 | 5.1 |
| Preparation Example No. of MES flakes | 5 | 1 | 3 | 13 | 15 | 10 |
| Mean particle diameter (mm) | 9.4 | 9.3 | 9.3 | 8.9 | 9.9 | 9.8 |
| Temperature in aging step (° C.) | 30 | 30 | 35 | 30 | 30 | 30 |
| Pressure in aging step (Pa) | 5000 | 5000 | 5000 | 5000 | 5000 | 5000 |

TABLE 2-continued

| | | | | | | |
|---|---|---|---|---|---|---|
| Aging period of time (days) | 14 | 14 | 14 | 14 | 14 | 14 |
| Ratio of endothermic peak area between 50° C. and 130° C. by DSC (%) | 72 | 93 | 87 | 81 | 70 | 65 |
| Determination method of caking properties | Simple* | Simple* | Simple* | Simple* | Simple* | Simple* |
| Number of drops | 6 | 0 | 0 | 8 | 6 | 7 |
| Rating of caking properties | ○ | ○○ | ○○ | ○ | ○ | ○ |

Simple*: Simple examination

Example 11

According to the method of test by use of flexible container bag, a polyethylene bag was set as an inner bag in a 430-L polypropylene flexible container bag (made by Furuta Shoten) and 200 kg of the MES flakes obtained in Preparation Example 4 was placed into the inner bag and allowed to stand at the temperature and the pressure as indicated in Table 3 for the period of time also as indicated in Table 3.

The DSC and the caking properties of the obtained solid fatty acid alkyl ester sulfonate metal salt were determined. The caking properties were determined based on the evaluation criterion of the test by use of flexible container bag. The results are shown in Table 3.

Comparative Example 3

The DSC and the caking properties of the MES flakes were determined in the same manner as in Example 11 except that the temperature at which the flakes were allowed to stand was changed to 20° C. The results are shown in Table 3.

TABLE 3

| | Comparative Example 3 | Example 11 |
|---|---|---|
| MES carbon chain length ratio C16/18 (mass ratio) | 90/10 | 90/10 |
| Water content (mass %) | 2.0 | 2.0 |
| Preparation Example No. of MES flakes | 4 | 4 |

TABLE 3-continued

| | Comparative Example 3 | Example 11 |
|---|---|---|
| Mean particle diameter (mm) | 9.2 | 9.2 |
| Temperature in aging step (° C.) | 20 | 30 |
| Pressure in aging step (Pa) | 5880 | 5880 |
| Aging period of time (days) | 7 | 28 |
| Ratio of endothermic peak area between 50° C. and 130° C. by DSC (%) | 7 | 85 |
| Determination method of caking properties | * | * |
| Rating of caking properties | x | ○○ |

*: Determination method by use of flexible container bag

Examples 12 to 15 and Comparative Examples 4 to 7

About 1 kg of the MES flakes obtained in Preparation Example 1, 3, 6 or 15 was placed into a 5-L polyethylene bag and allowed to stand at the temperature as indicated in Table 4 for the period of time also as indicated in Table 4 in an oven of forced convection type (DN-61, made by Yamato Scientific Co., Ltd.). After that, the flakes were cooled to room temperature and crushed with the hands to obtain the flakes.

The DSC and the caking properties of the obtained solid fatty acid alkyl ester sulfonate metal salt were determined.

The DSC and the caking properties of the obtained MES flakes were determined by the simple examination. The caking properties were determined by the simple examination. The melting point of the obtained MES flakes was determined by the method as in the "Determination of melting point, endotherm and exotherm by DSC" to be described later. The results are shown in Table 4.

TABLE 4

| | Comparative Example 4 | Example 12 | Comparative Example 5 | Example 13 | Comparative Example 6 | Example 14 | Comparative Example 7 | Example 15 |
|---|---|---|---|---|---|---|---|---|
| MES carbon chain length ratio C16/18 (mass ratio) | 99/1 | 99/1 | 90/10 | 90/10 | 80/20 | 80/20 | 45/55 | 45/55 |
| Water content (%) | 2.1 | 2.1 | 1.9 | 1.9 | 2.2 | 2.2 | 3.0 | 3.0 |
| Preparation Example No. of MES flakes | 1 | 1 | 3 | 3 | 6 | 6 | 15 | 15 |
| Mean particle diameter (mm) | 8.9 | 8.9 | 9.2 | 9.2 | 9.5 | 9.5 | 8.9 | 8.9 |
| Temperature in aging step (° C.) | 20 | 70 | 40 | 60 | 40 | 60 | 30 | 50 |
| Aging period of time (min.) | 120 | 20 | 120 | 30 | 120 | 120 | 600 | 360 |
| Ratio of endothermic peak area between 50° C. and 130° C. by DSC (%) | 5 | 88 | 21 | 56 | 15 | 54 | 1 | 89 |
| Melting point of crystalline MES | 82 | 89 | 84 | 89 | 75 | 81 | not detected** | 60 |
| Determination method of caking properties | Simple* | Simple* | Simple* | Simple* | Simple* | Simple* | Simple* | Simple* |
| Number of drops | 50 | 1 | 15 | 0 | 100 | 7 | 88 | 7 |
| Rating of caking properties | x | ○○ | x | ○○ | x | ○ | x | ○ |

Simple*: Simple examination

Not detected**: No melting point peak was observed. The melting point of 70° C. was found after storage at 45° C. for one week.

Examples 16 to 20 and Comparative Examples 8 to 12

The MES flakes obtained in Preparation Example 3, 6, 7, 8 or 9 were heated and turned into a melt having a temperature corresponding to the kneading temperature shown in Table 5. The melt was placed into a KRC kneader (Model S2, made by Kurimoto, Ltd.) at a feed rate of 600 to 800 g/min and kneaded at the shear rate as indicated in Table 5 for 0.5 minutes, with hot water of the kneading temperature as shown in Table 5 flowing through the jacket of the kneader. Then, the melt taken out of the kneader was sandwiched between stainless steel plates and cooled. The cooled product was crushed with the hands to obtain the flakes. The DSC and the caking properties of the obtained MES flakes were determined The caking properties were determined by the simple examination. The results are shown in Table 5.

Examples 21 to 25 and Comparative Examples 13 to 17

The MES flakes (1 kg) obtained in Preparation Example 5, 11, 12, 13 or 15 were subjected to aging (crystallization step) at the temperature and for the period of time as indicated in Table 6. The MES flakes thus obtained were pulverized in a speed mill (under the milling conditions that the number of revolutions was 1500 rpm, the screen pore diameter was 2.0 mm and the internal temperature of the mill was 25° C.). Then, 72 g of the MES powder thus obtained was mixed with 8 g of zeolite (aluminosilicate, "SILTON B" made by Mizusawa Industrial Chemicals, Ltd.), thereby obtaining a coated MES powder. The mean particle diameter of the obtained coated powder was determined, and the caking properties were measured according to the simple examination to be described later. The results are shown in Table 6. In Comparative Examples 13 to 17, the aging step (crystallization step) was not carried out. The content of coating agent shown in Table 6 is the amount of coating agent based on the mass of the MES powder.

TABLE 5

| | Comparative Example 8 | Example 16 | Comparative Example 9 | Example 17 | Comparative Example 10 |
|---|---|---|---|---|---|
| MES carbon chain length ratio C16/18 (mass ratio) | 99/1 | 99/1 | 90/10 | 90/10 | 80/20 |
| Water content (mass %) | 3.1 | 3.1 | 1.9 | 1.9 | 2.2 |
| Preparation Example No. of MES flakes | 9 | 9 | 3 | 3 | 6 |
| Mean particle diameter (mm) | 8.8 | 8.8 | 10.3 | 10.2 | 9.5 |
| Shear rate (s−1) | 50 | 200 | 450 | 450 | 450 |
| Kneading temperature (° C.) | 70 | 70 | 100 | 70 | 100 |
| Ratio of endothermic peak area between 50° C. and 130° C. by DSC (%) | 33 | 81 | 0 | 72 | 0 |
| Melting point of crystalline MES | 87 | 89 | 81 | 90 | 75 |
| Determination method of caking properties | Simple* | Simple* | Simple* | Simple* | Simple* |
| Number of drops | 40 | 1 | 100 or more | 1 | 89 |
| Rating of caking properties | x | ∘∘ | x | ∘∘ | x |

| | Example 18 | Comparative Example 11 | Example 19 | Comparative Example 12 | Example 20 |
|---|---|---|---|---|---|
| MES carbon chain length ratio C16/18 (mass ratio) | 80/20 | 60/40 | 60/40 | 45/55 | 45/55 |
| Water content (mass %) | 2.2 | 2.2 | 2.2 | 2.2 | 2.2 |
| Preparation Example No. of MES flakes | 6 | 7 | 7 | 8 | 8 |
| Mean particle diameter (mm) | 9.5 | 10.1 | 10.1 | 9.9 | 9.9 |
| Shear rate (s−1) | 450 | 450 | 450 | 450 | 450 |
| Kneading temperature (° C.) | 60 | 100 | 60 | 100 | 70 |
| Ratio of endothermic peak area between 50° C. and 130° C. by DSC (%) | 60 | 0 | 58 | 0 | 89 |
| Melting point of crystalline MES | 93 | not detected** | 69 | not detected** | 74 |
| Determination method of caking properties | Simple* | Simple* | Simple* | Simple* | Simple* |
| Number of drops | 7 | 100 or more | 7 | 100 or more | 7 |
| Rating of caking properties | ∘ | x | ∘ | x | ∘ |

Not detected**: No melting point peak was observed. The melting points of 62° C. and 75° C. were respectively found in Comparative Examples 11 and 12 after storage at 45° C. for one week.
Simple*: Simple examination

TABLE 6

|  | Comparative Example 13 | Example 21 | Comparative Example 14 | Example 22 | Comparative Example 15 |
|---|---|---|---|---|---|
| MES carbon chain length ratio C16/18 (mass ratio) | 100/0 | 100/0 | 90/10 | 90/10 | 80/20 |
| Water content (%) | 1.7 | 1.7 | 3.0 | 3.0 | 3.2 |
| Preparation Example No. of MES flakes | 11 | 11 | 5 | 5 | 12 |
| Mean particle diameter of flakes (mm) | 9.2 | 9.2 | 2.0 | 5.0 | 9.4 |
| Temperature in aging step for flakes (° C.) | no aging | 30 | no aging | 30 | no aging |
| Pressure in aging step for flakes (Pa) | no aging | 5000 | no aging | 5000 | no aging |
| Aging period of time for flakes (days) | no aging | 14 | no aging | 14 | no aging |
| Ratio of endothermic peak area between 50° C. and 130° C. by DSC (%) | 17 | 79 | 0 | 72 | 12 |
| Kind of coating agent | zeolite | zeolite | zeolite | zeolite | zeolite |
| Content of coating agent (mass %) | 10 | 10 | 10 | 10 | 10 |
| Mean particle diameter of coated MES powder (μm) | 478 | 490 | 453 | 441 | 532 |
| Temperature of ground product (° C.) during storage | 40 | 40 | 40 | 40 | 40 |
| Storage period of ground product (days) | 7 | 7 | 7 | 7 | 7 |
| Determination method of caking | Simple* | Simple* | Simple* | Simple* | Simple* |
| Number of drops | 77 | 9 | 100 or more | 4 | 100 or more |
| Rating of caking properties | x | ○ | x | ○○ | x |

|  | Example 23 | Comparative Example 16 | Example 24 | Comparative Example 17 | Example 25 |
|---|---|---|---|---|---|
| MES carbon chain length ratio C16/18 (mass ratio) | 80/20 | 60/40 | 60/40 | 45/55 | 45/55 |
| Water content (%) | 3.2 | 3.0 | 3.0 | 3.0 | 3.0 |
| Preparation Example No. of MES flakes | 12 | 13 | 13 | 15 | 15 |
| Mean particle diameter of flakes (mm) | 9.4 | 9.4 | 9.4 | 9.3 | 9.3 |
| Temperature in aging step for flakes (° C.) | 30 | no aging | 30 | no aging | 30 |
| Pressure in aging step for flakes (Pa) | 5000 | no aging | 5000 | no aging | 5000 |
| Aging period of time for flakes (days) | 28 | no aging | 28 | no aging | 28 |
| Ratio of endothermic peak area between 50° C. and 130° C. by DSC (%) | 70 | 0 | 72 | 0 | 81 |
| Kind of coating agent | zeolite | zeolite | zeolite | zeolite | zeolite |
| Content of coating agent (mass %) | 10 | 10 | 10 | 10 | 10 |
| Mean particle diameter of coated MES powder (μm) | 550 | 403 | 397 | 783 | 751 |
| Temperature of ground product (° C.) during storage | 40 | 40 | 40 | 40 | 40 |
| Storage period of ground product (days) | 7 | 7 | 7 | 7 | 7 |
| Determination method of caking | Simple* | Simple* | Simple* | Simple* | Simple* |
| Number of drops | 2 | 100 or more | 6 | 100 or more | 8 |
| Rating of caking properties | ○○ | x | ○ | x | ○ |

Simple*: Simple examination

Examples 26 to 30 and Comparative Examples 18 to 22

Granular detergent compositions where the MES powder was incorporated were obtained in the manner as shown below.

Preparation Example 18

Preparation of Granular Detergent Composition (1)

(Slurry Preparation Step)

Water of 25° C. was placed into a blender with an effective capacity of 700 L, provided with a two-stage 45°-pitched paddle type impeller (with an impeller length of 640 mm and an impeller width of 65 mm) and two baffles (having a length of 600 mm and a width of 50 mm, with a clearance of 30 mm between the baffle and the wall surface). With the pitched paddle impeller being rotated at 120 rpm (for stirring until the addition of the components was completed), builders, i.e., sodium silicate, poly(sodium acrylate), sodium sulfate, sodium tripolyphosphate (STPP), and sodium carbonate were added in this order. With stirring the mixture, steam of 0.1 MPa (in terms of gauge pressure) or cold water of 8° C. was allowed to pass through the jacket of the blender to control the slurry temperature at 50° C. The stirring was continued for another one hour while the slurry was maintained at the above-mentioned temperature. Thus, 600 kg of a slurry with a water content of about 42% was prepared.

(Spray-Drying Step)

Subsequently, the slurry was fed to a counter-flow-type dryer tower with a tower diameter of 2.0 m and an effective length of 5.6 m at a feed rate of 400 kg/h., and sprayed from the top of the tower using a pressure nozzle, thereby obtaining spray-dried granules. The spraying operation was carried out under a spraying pressure of 2 to 3.5 MPa using the same nozzle as described in Example 2 of JP Kokai No. Hei 9-75786. The temperature of heated air in the drying tower was 300° C. and the exhaust rate was 240 m³/min. The water content of the obtained spray-dried granules was 3.9%. The composition of the obtained spray-dried granules is shown in Table 7.

TABLE 7

| Components | Contents Mass (%) |
|---|---|
| STPP | 17.2 |
| Na silicate | 8.6 |
| Poly(Na acrylate) | 1.8 |
| Na sulfate | 34.8 |
| Na carbonate | 33.8 |
| Water content | 3.9 |
| Total | 100 |

(Preparation of Granular Detergent Composition)

The spray-dried granules obtained through the above-mentioned spray-drying step (thereafter, cooled to room temperature), an enzyme, a bleaching agent, a bleaching activator and the MES powder were charged into a polyethylene bag so that the each component might be contained in such an amount (mass %) as shown in Table 8. (The above-mentioned MES powder was obtained in such a manner that the MES flakes or MES particles (120 cm$^3$) each prepared in Preparation Example as shown in Table 1 were charged into a cell with a diameter of 50 mm and a length of 100 mm, subjected to aging (crystallization step) at the flake aging temperature for the flake aging time as indicated in Table 8, under pressure of 5000 Pa to the upper part of the cell, and then pulverized in a speed mill (with the internal temperature of the mill maintained at 35° C.).) The components in the polyethylene bag were mixed by manually shaking the bag up and down 30 times. After that, a perfume in such an amount (mass %) as shown in Table 8 was sprayed to give the detergent particles a fragrance, so that a granular detergent composition was obtained. The fluidity of the composition was evaluated according to the method in "Evaluation of fluidity of granular detergent composition" to be described later. The results are shown in Table 8. The item "Amount of MES powder" in Table 8 indicates the content of MES based on the mass of the granular detergent composition. The item "Mean particle diameter of MES" in Table 8 indicates the mean particle diameter of the MES powder determined according to the method in "Determination of mean particle diameter" to be described later. In Comparative Examples 18 to 22, the MES flakes were not subjected to the aging step (crystallizing step).

TABLE 8

| | Comparative Example 18 | Example 26 | Comparative Example 19 | Example 27 | Comparative Example 20 |
|---|---|---|---|---|---|
| MES carbon chain length ratio C16/18 (mass ratio) | 99/1 | 99/1 | 90/10 | 90/10 | 80/20 |
| Water content (%) | 5.1 | 5.1 | 3.0 | 3.0 | 2.2 |
| Preparation Example No. of MES flakes | 10 | 10 | 5 | 5 | 6 |
| Spray-dried granules (mass %) | 82.2 | 82.2 | 82.2 | 82.2 | 77.2 |
| Perfume (mass %) | 0.2 | 0.2 | 0.2 | 0.2 | 0.2 |
| Enzyme (mass %) | 0.8 | 0.8 | 0.8 | 0.8 | 0.8 |
| Bleaching agent (mass %) | 6 | 6 | 6 | 6 | 6 |
| Bleaching activator (mass %) | 0.8 | 0.8 | 0.8 | 0.8 | 0.8 |
| Amount of MES powder (mass %) | 10 | 10 | 10 | 10 | 15 |
| Temperature in aging step for flakes (° C.) | no aging | 30 | no aging | 30 | no aging |
| Pressure in aging step for flakes (Pa) | no aging | 5000 | no aging | 5000 | no aging |
| Aging period of time for flakes (days) | no aging | 28 | no aging | 28 | no aging |
| Mean particle diameter of MES powder (μm) | 455 | 455 | 483 | 483 | 491 |
| Storage temperature of detergent composition (° C.) | 45 | 45 | 45 | 45 | 45 |
| Storage period of detergent composition (days) | 7 | 7 | 7 | 7 | 7 |
| Ratio of endothermic peak area between 50° C. and 130° C. by DSC (%) | 0 | 59 | 0 | 88 | 0 |
| Evaluation of fluidity of granular detergent composition (%) | 67 | 79 | 68.2 | 80.6 | 61.2 |

| | Example 28 | Comparative Example 21 | Example 29 | Comparative Example 22 | Example 30 |
|---|---|---|---|---|---|
| MES carbon chain length ratio C16/18 (mass ratio) | 80/20 | 60/40 | 60/40 | 45/55 | 45/55 |
| Water content (%) | 2.2 | 3.0 | 3.0 | 2.0 | 2.0 |
| Preparation Example No. of MES flakes | 6 | 13 | 13 | 14 | 14 |
| Spray-dried granules (mass %) | 77.2 | 82.2 | 82.2 | 82.2 | 82.2 |
| Perfume (mass %) | 0.2 | 0.2 | 0.2 | 0.2 | 0.2 |
| Enzyme (mass %) | 0.8 | 0.8 | 0.8 | 0.8 | 0.8 |
| Bleaching agent (mass %) | 6 | 6 | 6 | 6 | 6 |
| Bleaching activator (mass %) | 0.8 | 0.8 | 0.8 | 0.8 | 0.8 |
| Amount of MES powder (mass %) | 15 | 10 | 10 | 10 | 10 |
| Temperature in aging step for flakes (° C.) | 30 | no aging | 30 | no aging | 30 |
| Pressure in aging step for flakes (Pa) | 5000 | no aging | 5000 | no aging | 5000 |
| Aging period of time for flakes (days) | 28 | no aging | 28 | no aging | 28 |
| Mean particle diameter of MES powder (μm) | 491 | 511 | 511 | 489 | 489 |
| Storage temperature of detergent composition (° C.) | 45 | 45 | 45 | 45 | 45 |
| Storage period of detergent composition (days) | 7 | 7 | 7 | 7 | 7 |

TABLE 8-continued

| | | | | | |
|---|---|---|---|---|---|
| Ratio of endothermic peak area between 50° C. and 130° C. by DSC (%) | 87 | 0 | 72 | 0 | 76 |
| Evaluation of fluidity of granular detergent composition (%) | 76.2 | 67 | 80.2 | 68.2 | 78.2 |

Examples 31 to 40 and Comparative Examples 23 to 26

The solid fatty acid alkyl ester sulfonate metal salt made from the MES flakes of each Preparation Example was pulverized to obtain a powder (MES powder) of the above-mentioned solid material.

Table 9 shows Preparation Example number of the MES flakes as the raw material for the solid fatty acid alkyl ester sulfonate metal salt used in each Example and Comparative Example, and the crystallization step employed. Table 9 also shows the ratio of the endothermic peak area of the obtained MES solid material between 50° C. and 130° C. when determined by the DSC.

The crystallization steps (I) to (III) shown in Table 9 are as follows:

(I) An inner bag made from polyethylene was set in a 430-L polypropylene flexible container bag (made by Furuta Shoten), and 200 kg of the MES flakes prepared in Preparation Example 1, 3, 4, 6, 13, 16 or 17 was placed into the inner bag. A weight (a $Na_2SO_4$-filled flexible container bag) was put on the MES flakes-filled container bag so that a pressure of 5880 Pa was exerted on the bottom surface of the MES flakes-filled bag. The MES flakes-filled bag was allowed to stand at the temperature and the pressure as indicated in Table 9 for the period of time as indicated in Table 9.

(II) The MES flakes prepared in Preparation Example 4, 6 or 14 were allowed to stand at the temperature as indicated in Table 9 for the period of time as shown in Table 9. After that, the flakes were cooled to room temperature and crushed with the hands to obtain the flakes.

(III) The MES flakes prepared in Preparation Example 3 or 6 were heated and turned into a melt having a temperature corresponding to the kneading temperature shown in Table 9. The melt was placed into a KRC kneader (Model S2, made by Kurimoto, Ltd.) at a feed rate of 600 to 800 g/min, and kneaded at the shear rate as indicated in Table 9 for 0.5 minutes, with hot water of the kneading temperature as indicated in Table 9 flowing through the jacket of the kneader. Then, the melt taken out of the kneader was sandwiched between stainless steel plates and cooled. The cooled product was crushed with the hands to obtain the flakes. Table 9 shows the kneading temperature and the shear rate.

To pulverize the MES solid material, the solid fatty acid alkyl ester sulfonate metal salt obtained through the above-mentioned step was fed into a pulverizer (Fitzmill, model DKA-3 made by Hosokawa Micron Corporation) and pulverized at a throughput of 180 kg/hr. The number of revolutions and the peripheral speed of the pulverizer, the internal temperature of the pulverizer during the pulverizing operation, and the screen pore diameter are shown in Table 9. To determine the temperature of the inside of the pulverizer, a sensor with a digital thermometer was inserted in the pulverizer at a position where the powder was just discharged from the screen and the temperature of the powder immediately after pulverized was read. The results based on the evaluation items "Observation of powder adhesion to pulverizer" and "Determination of particle size distribution" are shown in Table 9. The mass frequency distribution by sieves with different openings is shown in Table 11, using the powders of Example 31 and Comparative Example 23.

TABLE 9

| | | Example 31 | Example 32 | Example 33 | Example 34 | Example 35 | Example 36 | Example 37 |
|---|---|---|---|---|---|---|---|---|
| Preparation Example No. of MES flakes | | 6 | 1 | 16 | 3 | 17 | 4 | 6 |
| Crystallization step | | (I) | (I) | (I) | (I) | (I) | (II) | (III) |
| (I) Aging | Temperature (° C.) | 30 | 35 | 30 | 35 | 35 | | |
| | Pressure (Pa) | 5880 | 5880 | 5880 | 5880 | 5880 | | |
| | Aging period (days) | 28 | 14 | 14 | 14 | 28 | | |
| (II) Temperature retention | Temperature (° C.) | | | | | | 75 | |
| | Period of time (min) | | | | | | 10 | |
| (III) Kneading | Kneading temperature (° C.) | | | | | | | 75 |
| | Shear rate (s−1) | | | | | | | 450 |
| Ratio of endothermic peak area between 50° C. and 130° C. by DSC (%) | | 87 | 98 | 66 | 87 | 99 | 91 | 95 |
| Internal temperature of pulverizer at pulverization (° C.) | | 35 | 35 | 35 | 35 | 35 | 35 | 35 |
| No. of revolutions of pulverizer (rpm) | | 2835 | 3402 | 3402 | 2835 | 2835 | 3969 | 2835 |
| Peripheral speed (m/s) | | 39 | 46.9 | 46.9 | 39 | 39 | 54.8 | 39 |
| Screen pore diameter (mmφ) | | 3 | 3 | 2 | 2 | 3 | 3 | 2 |
| Powder adhesion to pulverizer | | ∘∘ | ∘∘ | ∘∘ | ∘∘ | ∘∘ | ∘∘ | ∘∘ |
| 1000 μm on | | ∘∘ | ∘∘ | ∘ | ∘∘ | ∘∘ | ∘∘ | ∘ |
| 149 μm pass | | ∘ | ∘∘ | ∘ | ∘ | ∘ | ∘∘ | ∘∘ |

| | | Example 38 | Example 39 | Example 40 | Comp. Example 23 | Comp. Example 24 | Comp. Example 25 | Comp. Example 26 |
|---|---|---|---|---|---|---|---|---|
| Preparation Example No. of MES flakes | | 3 | 13 | 14 | 16 | 4 | 6 | 3 |
| Crystallization step | | (III) | (I) | (II) | (I) | (I) | (II) | (III) |
| (I) Aging | Temperature (° C.) | | 30 | | 25 | 20 | | |
| | Pressure (Pa) | | 5880 | | 5880 | 5880 | | |

TABLE 9-continued

|  |  |  |  |  |  |  |  |
|---|---|---|---|---|---|---|---|
| (II) Temperature retention | Aging period (days) |  | 28 | 14 | 7 |  |  |
|  | Temperature (° C.) |  |  | 75 |  | 75 |  |
|  | Period of time (min) |  |  | 10 |  | 2 |  |
| (III) Kneading | Kneading temperature (° C.) | 75 |  |  |  |  | 75 |
|  | Shear rate (s−1) | 450 |  |  |  |  | 60 |
| Ratio of endothermic peak area between 50° C. and 130° C. by DSC (%) |  | 88 | 80 | 85 | 28 | 7 | 22 | 21 |
| Internal temperature of pulverizer at pulverization (° C.) |  | 45 | 35 | 35 | 35 | 35 | 35 | 45 |
| No. of revolutions of pulverizer (rpm) |  | 3969 | 3402 | 2835 | 3402 | 3969 | 3969 | 3969 |
| Peripheral speed (m/s) |  | 54.8 | 46.9 | 39 | 46.9 | 54.8 | 54.8 | 54.8 |
| Screen pore diameter (mmφ) |  | 3 | 3 | 3 | 3 | 2 | 3 | 3 |
| Powder adhesion to pulverizer |  | ○○ | ○ | ○ | Δ | x | Δ | x |
| 1000 μm on |  | ○ | ○ | ○ | ○ | ○○ | ○ | ○○ |
| 149 μm pass |  | ○ | ○○ | ○○ | ○○ | ○ | x | Δ |

Examples 41 to 43 and 47 to 49, and Comparative Examples 27 and 28

The powder of the solid fatty acid alkyl ester sulfonate metal salt was obtained in the same manner as in Examples 31 to 40 except that an inorganic powder was fed into the Fitzmill together with the solid fatty acid alkyl ester sulfonate metal salt. The crystallization step employed, the kind and amount of inorganic powder, the internal temperature of the pulverizer during the pulverizing operation, and the screen pore diameter are listed in Table 10. Table 10 also shows the results. The mass frequency distribution of the powder of Example 42 by sieves with different openings is shown in Table 11.

Examples 44 to 46 and 50, and Comparative Example 29

The powder of the solid fatty acid alkyl ester sulfonate metal salt was obtained in the same manner as in Examples 31 to 40 except that after the solid fatty acid alkyl ester sulfonate metal salt was pulverized in the Fitzmill, an inorganic powder was mixed together with the obtained MES powder. The ratio of the endothermic peak area of the obtained MES solid material between 50° C. and 130° C. when determined by the DSC, the crystallization step employed, the kind and amount of inorganic powder, the internal temperature of the pulverizer during the pulverizing operation, the number of revolutions and the peripheral speed of the pulverizer and the screen pore diameter are shown in Table 10. Table 10 also shows the results.

TABLE 10

|  |  | Example 41 | Example 42 | Example 43 | Example 44 | Example 45 | Example 46 | Example 47 |
|---|---|---|---|---|---|---|---|---|
| Preparation Example No. of MES flakes |  | 6 | 16 | 3 | 17 | 3 | 4 | 6 |
| Crystallization step |  | (I) | (I) | (I) | (I) | (II) | (II) | (III) |
| (I) Aging | Temperature (° C.) | 30 | 30 | 35 | 30 |  |  |  |
|  | Pressure (Pa) | 5880 | 5880 | 5880 | 5880 |  |  |  |
|  | Aging period (days) | 28 | 14 | 14 | 21 |  |  |  |
| (II) Temp. retention | Temperature (° C.) |  |  |  |  | 75 | 75 |  |
|  | Period of time (min) |  |  |  |  | 10 | 10 |  |
| (III) Kneading | Kneading temperature (° C.) |  |  |  |  |  |  | 75 |
|  | Shear rate (s−1) |  |  |  |  |  |  | 450 |
| Ratio of endothermic peak area between 50° C. and 130° C. by DSC (%) |  | 87 | 66 | 87 | 97 | 82 | 91 | 95 |
| Internal temp. of pulverizer at pulverization (° C.) |  | 35 | 35 | 45 | 30 | 35 | 35 | 35 |
| No. of revolutions of pulverizer (rpm) |  | 3969 | 3969 | 3969 | 2835 | 3402 | 3402 | 2835 |
| Peripheral speed (m/s) |  | 54.8 | 54.8 | 54.8 | 39 | 46.9 | 46.9 | 39 |
| Screen pore diameter (mmφ) |  | 3 | 3 | 2 | 2 | 2 | 3 | 2 |
| Kind of inorganic powder (*1) |  | A | B | C | A | B | A | C |
| Time for mixing of inorganic powder (*2) |  | 1 | 1 | 1 | 2 | 2 | 2 | 1 |
| Powder adhesion to pulverizer |  | ○○ | ○○ | ○○ | ○○ | ○○ | ○○ | ○○ |
| 1000 μm on |  | ○○ | ○ | ○ | ○ | ○○ | ○○ | ○○ |
| 149 μm pass |  | ○ | ○○ | ○ | ○○ | ○ | ○○ | ○○ |

|  |  | Example 48 | Example 49 | Example 50 | Comp. Example 27 | Comp. Example 28 | Comp. Example 29 |
|---|---|---|---|---|---|---|---|
| Preparation Example No. of MES flakes |  | 1 | 13 | 14 | 6 | 3 | 3 |
| Crystallization step |  | (III) | (III) | (I) | (II) | (III) | (III) |
| (I) Aging | Temperature (° C.) |  |  | 30 |  |  |  |
|  | Pressure (Pa) |  |  | 5880 |  |  |  |
|  | Aging period (days) |  |  | 28 |  |  |  |
| (II) Temp. retention | Temperature (° C.) |  |  |  | 75 |  |  |
|  | Period of time (min) |  |  |  | 2 |  |  |
| (III) Kneading | Kneading temperature (° C.) | 75 | 75 |  |  | 80 | 75 |
|  | Shear rate (s−1) | 450 | 450 |  |  | 40 | 60 |

TABLE 10-continued

| | | | | | | |
|---|---|---|---|---|---|---|
| Ratio of endothermic peak area between 50° C. and 130° C. by DSC (%) | 88 | 87 | 78 | 22 | 12 | 23 |
| Internal temp. of pulverizer at pulverization (° C.) | 35 | 35 | 35 | 35 | 30 | 45 |
| No. of revolutions of pulverizer (rpm) | 2835 | 3402 | 2835 | 2835 | 2835 | 3402 |
| Peripheral speed (m/s) | 39 | 46.9 | 39 | 39 | 39 | 46.9 |
| Screen pore diameter (mmφ) | 2 | 3 | 2 | 2 | 2 | 2 |
| Kind of inorganic powder (*1) | A | A | C | B | A | A |
| Time for mixing of inorganic powder (*2) | 1 | 1 | 2 | 1 | 1 | 2 |
| Powder adhesion to pulverizer | ○○ | ○○ | ○○ | Δ | ○○ | x |
| 1000 μm on | ○○ | ○○ | ○○ | ○○ | Δ | ○○ |
| 149 μm pass | ○ | ○○ | ○ | ○○ | Δ | ○ |

(*1) Inorganic powder (Blank: no inorganic powder to be mixed, A: zeolite A type, B: Sodium sulfate, C: sodium carbonate) Content: 10 mass %
A: zeolite A type, tradename SILTON B, made by Mizusawa Industrial Chemicals, Ltd., with a bulk density of 0.30 g/cm3 and a mean particle diameter of 1 to 5 μm
B: sodium sulfate: neutral anhydrous fine powder (industrial grade), made by Shikoku Chemicals Corporation, with a mean particle diameter of 40 to 50 μm
C: sodium carbonate [2]: made by Asahi Glass Co., Ltd., by grinding granular ash (with a purity of 99%, a bulk density of 1.07 g/cm3 and a mean particle diameter of 200 to 400 μm) to have a mean particle diameter of 80 μm
(*2) 1: Mixing of inorganic powder during grinding of MES. 2: Mixing of inorganic powder after grinding of MES.

TABLE 11

| Opening of Sieve (μm) | Example 31 | Example 42 | Comp. Ex. 23 |
|---|---|---|---|
| | Mass frequency (%) | | |
| 1410 on | 1.8 | 2.0 | 2.6 |
| 1190 on | 2.0 | 2.2 | 3.2 |
| 1000 on | 3.6 | 4.5 | 6.2 |
| 710 on | 13.9 | 12.0 | 11.6 |
| 500 on | 17.1 | 16.9 | 14.8 |
| 350 on | 17.0 | 16.4 | 15.2 |
| 250 on | 25.3 | 22.9 | 20.1 |
| 149 on | 15.2 | 14.9 | 14.2 |
| 149 pass | 4.1 | 8.2 | 12.1 |
| Mean particle diameter (μm) | 432 | 415 | 411 |

Examples 51 and 52

Preparation Example 19

Preparation of Granular Detergent Composition (2)

(Slurry Preparation Step)

In the same manner as in Preparation Example 18, water of 25° C. was placed into a blender with an effective capacity of 700 L, provided with a two-stage 45°-pitched paddle type impeller (with an impeller length of 640 mm and an impeller width of 65 mm) and two baffles (having a length of 600 mm and a width of 50 mm, with a clearance of 30 mm between the baffle and the wall surface). Sodium hydroxide was added to water and dissolved therein while the impeller was rotated at 120 rpm. (The stirring operation was continued until the addition of the components was completed). Then, LAS-H was added for neutralization, thereby generating LAS-Na ("LAS-Na" in Table 12 indicates the amount thereof generated after neutralization by the reaction of LAS-H with sodium hydroxide. Generated LAS-Na:sodium hydroxide added: LAS-H added=10.00:1.25:9.36 (ratio by mass)). Subsequently, builders, i.e., sodium silicate, poly(sodium acrylate), sodium sulfate, sodium tripolyphosphate (STPP) and sodium carbonate were added in this order. With stirring the mixture, steam of 0.1 MPa (in terms of gauge pressure) or cold water of 8° C. was allowed to pass through the jacket of the blender to control the slurry temperature to 50° C. The stirring was continued for another one hour at the above-mentioned temperature. Thus, 600 kg of a slurry with a water content of 42% was prepared.

(Spray-Drying Step)

Then, the slurry was fed to a counter-flow-type dryer tower with a tower diameter of 2.0 m and an effective length of 5.6 m at a feed rate of 400 kg/hr., and sprayed from the top of the tower using a pressure nozzle, thereby obtaining spray-dried granules. The spraying operation was carried out under a spraying pressure of 2 to 3.5 MPa using the same nozzle as that described in Example 2 of JP Kokai No. Hei 9-75786. The temperature of heated air in the drying tower was 300° C. and the exhaust rate was 240 m$^3$/min. The water content of the obtained spray-dried granules was 4.0%.

(Preparation of Granular Detergent Composition)

The obtained spray-dried granules (cooled to room temperature), an enzyme, a bleaching agent, a bleaching activator and the MES powder obtained in Example 31 in such amounts (mass %) as indicated in Table 12 were charged into a horizontal drum-shaped tumbling mixer (with a drum diameter of 585 mm and a drum length of 490 mm, having a 131.7-L container equipped with two 45-mm-high baffles installed with a clearance of 20 mm from the inner wall surface of the drum) at a powder filling rate of 30%. While mixing the obtained detergent granules at 22 rpm and at 25° C., a perfume in such an amount (mass %) as indicated in Table 12 was sprayed to give the detergent granules a fragrance. Thus, granular detergent compositions as shown in Table 12 were obtained in Examples 51 and 52. In Table 12, "MES-Na (α-SF-Na)" is a powder of the solid fatty acid alkyl ester sulfonate metal salt obtained in Example 31; and the item "Other components in small contents" means a total of the by-products and the like derived from each of the raw materials.

TABLE 12

| | Mass (%) | |
|---|---|---|
| Composition | Example 51 | Example 52 |
| MES-Na(α-SF-Na) | 7.22 | 8.02 |
| LAS-Na | 7.22 | 8.02 |
| STPP | 14.44 | 16.04 |
| Na silicate | 7.22 | 8.02 |
| Poly(Na acrylate) | 1.44 | 1.60 |
| Na sulfate | 29.21 | 32.45 |
| Na carbonate | 20.83 | 12.03 |
| Water content | 3.61 | 4.01 |

TABLE 12-continued

| | Mass (%) | |
|---|---|---|
| Composition | Example 51 | Example 52 |
| Other components in small contents | 1.01 | 1.12 |
| Perfume | 0.20 | 0.22 |
| Enzyme | 0.80 | 0.89 |
| Bleaching agent | 6.00 | 6.67 |
| Bleaching activator | 0.80 | 0.89 |
| Total | 100 | 100 |

Evaluation Methods
Determination of melting point, endotherm and exotherm by DSC As the differential scanning calorimeter, Diamond DSC (Perkin Elmer Inc.) was employed. Using a blender (Trio Blender, made by Trio Science CO. LTD.), 20 g of the MES flakes obtained in each of Examples and Comparative Examples was pulverized, and then an aluminum pan holding 5 to 30 mg of the pulverized MES flakes thereon was set in the calorimeter and heated from 0° C. to 130° C. at a heating rate of 2° C./min to determine the melting point, endotherm and exotherm. The melting point of the metastable solid is defined as a temperature corresponding to the top of the maximum peak. To obtain the melting point of the crystalline MES, the appropriate sample in a cell was subjected to the same determination by DSC as mentioned above after stored at 45° C. for one week. In this case, the melting point is regarded as a temperature corresponding to the peak top of a peak appearing at the highest temperature among the peaks of which intensities are 10% or more (in terms of the ratio by peak height) relative to that of the maximum peak. In the above-mentioned process, the endotherm between 50° C. and 130° C. is supposed to A, and the whole endotherm between 0° C. and 130° C. is supposed to B, and a value is calculated according to the formula (A/B)×100.

If the exothermic peak is observed within a range of 100° C. or less, the absolute value of exotherm is subtracted from the endotherm over 50° C. to obtain the value A. Similarly, the value B is regarded as the total endotherm obtained by subtracting the absolute value of the exotherm of exothermic peak from the endotherm of endothermic peak.

Evaluation of Caking Properties
<Simple Examination>

The simple examination was carried out by following the procedure shown below.

In Examples 1 to 10 and Comparative Example 2, the simple examination was carried out after completion of the following operation (for conversion into the crystalline MES) corresponding to the above-mentioned step (I).
—Operation Corresponding to the Above-Mentioned Step (I)—

The MES flakes or MES particles (120 cm³) prepared in each Preparation Example shown in Table 1 were charged into a cell with a diameter of 50 mm and a length of 100 mm, subjected to aging at the temperature for the period of time as indicated in Table 2, with the application of a pressure of 5000 Pa to the upper part of the cell.
—Simple Examination—

With the application of a load of 10,000 Pa to the upper part of the cell, the cell holding therein each sample obtained from the above-mentioned aging step; or the cell (with a diameter of 50 mm and a length of 100 mm) holding therein 120 cm³ of the MES flakes of Comparative Example 1 not subjected to the above-mentioned aging step, the MES flakes obtained from the step for conversion into the crystalline MES, corresponding to the step (II) as shown in Table 4 and corresponding to the step (III) as shown in Table 5, or the MES powders shown in Table 6 was stored in a constant temperature bath of 45° C. (or 40° C. in the case of the MES powders shown in Table 6) for one week to form a cake. The cake thus formed was put into a sieve with an opening of 16 mm (or 4.75 mm in the case of the MES powders shown in Table 6) and the sieve was dropped from a height of 10 mm. The number of drops required for breaking the cake, with not adhesion of flakes to each other (or passing the whole powder through the sieve in the case of the MES powders shown in Table 6) was determined. The number of drops was taken as an indicator to evaluate the caking properties based on the following criterion.
<Evaluation Criterion>
oo: The number of drops was 5 or less.
o: The number of drops was 6 or more and 9 or less.
x: The number of drops was 10 or more.

According to the invention, the caking properties during the storage rated as "o" and "oo" were considered acceptable.
<Test by Use of Flexible Container Bag>

In Example 11 and Comparative Example 3, the test by use of flexible container bag was carried out after completion of the following operation (for conversion into the crystalline MES) corresponding to the above-mentioned step (I).
—Operation Corresponding to the Above-Mentioned Step (I)—

The MES flakes prepared in Example 11 or Comparative Example 3 were placed into a flexible container bag. A weight (a Na$_2$SO$_4$-filled flexible container bag) was put on the MES flakes-filled container bag so that a pressure of 5880 Pa was exerted on the bottom surface of the MES flakes-filled bag. The MES flakes-filled bag was kept in a constant temperature booth for aging ("Carry Pack", made by Nissoku Engineering Co., Ltd.) at the temperature for the period of time as indicated in Table 3.
—Test by Use of Flexible Container Bag—

After the above-mentioned aging step, the above-mentioned weight (the Na$_2$SO$_4$-filled flexible container bag) was changed so that the pressure of 11760 Pa might be exerted, and the MES flakes-filled bag was allowed to stand in the above-mentioned booth for aging at 45° C. for one week. Then, the MES flakes were discharged from the outlet at the lower part of the container bag. By observing the discharging condition, the caking properties were evaluated based on the following criterion.
<Evaluation Criterion>
oo: spontaneously discharged.
o: spontaneously discharged, but some cakes were observed.
x: not spontaneously discharged, but discharged with the aid of externally applied impact and pressure.
<Evaluation of Fluidity of Granular Detergent Composition>

In a cell with a diameter of 50 mm and a height of 100 mm where cuts made in advance were joined with a heat-resistant tape (masking tape), as shown in FIG. 7, 50 g of the granular detergent composition obtained in each of Examples 26 to 30 and Comparative Examples 18 to 22 (Table 8) was placed. The cell was tightly sealed in a polyethylene bag and allowed to stand under a load of 10,000 Pa in a constant temperature bath of 45° C. for two days. After that, the cell was gently put on a sieve with an opening of 16 mm on a tray, and the heat-resistant tape was peeled off to gently remove the peripheral plates of the cell. Part of the granules collapsed and fell to the tray. The mass of the granules falling onto the tray was measured using an electrobalance. The powder fluidity was evaluated in terms of the ratio by mass (unit: %) of the portion falling down to the tray relative to the total mass of powder.

<Observation of Powder Adhesion to Pulverizer>

The pulverizer was disassembled and the adhesion of powder to the pulverizer was visually observed. The adhesion of powder was evaluated according to the following criterion. The results are shown in Tables 9 and 10.

oo: No adhesion was observed.

Δ: The pulverizer was not clogged with the powder, but powder adhered to the pulverizer.

x: The pulverizer got clogged with powder.

<Determination of Particle Size Distribution of Powders of Less than 3 mm>

The particle size distribution of powder made from solid fatty acid alkyl ester sulfonate metal salt obtained in each of Examples 21 to 50 and Comparative Example 13 to 29 was determined.

The particle size distribution was determined by calculating the mass frequency (%) of powders in the following manner:

Classification was conducted using a classifier including nine sieves with the respective openings of 1680, 1410, 1190, 1000, 710, 500, 350, 250 and 149 μM, and a saucer. For the classification, above the saucer the sieves were stacked on top of each other in ascending order of opening, and 100 g of a sample of spray-dried granules was placed into the uppermost sieve of 1680 μm and the lid was closed. The classifier was set in the Ro-Tap sieve shaker (made by Iida-seisakusho Japan Corporation, 156 tappings/min, 290 rollings/min) and oscillations were applied to the classifier for 10 minutes. After that, the sample granules remaining on each sieve and the saucer were individually collected.

By repeating the above-mentioned procedure, a sample classified according to the particle size, i.e., 1410 to 1680 μm (1410 μm on), 1190 to 1410 μm (1190 μm on), 1000 to 1190 μm (1000 μm on), 1000 to 710 μm (710 μm on), 500 to 710 μm (500 μm on), 350 to 500 μm (350 μm on), 250 to 350 μm (250 μm on), 149 to 250 μm (149 μm on), and the saucer to 149 μm (149 μm pass) was obtained, and then the mass frequency percent (%) was calculated.

The obtained results were rated based on the following criterion.

In terms of coarse powders ("1000 μm on" in Tables 9 and 10):

oo: The mass frequency (%) of "1000 μm on" was 8% or less.

o: The mass frequency (%) of "1000 μm on" was more than 8% and 10% or less.

Δ: The mass frequency (%) of "1000 μm on" was more than 10% and 12% or less.

x: The mass frequency (%) of "1000 μm on" was more than 12%.

In terms of fine powders ("149 μm pass" in Tables 9 and 10):

oo: The mass frequency (%) of "149 μm pass" was 8% or less.

o: The mass frequency (%) of "149 μm pass" was more than 8% and 10% or less.

Δ: The mass frequency (%) of "149 μm pass" was more than 10% and 12% or less.

x: The mass frequency (%) of "149 μm pass" was more than 12%.

In the above, when the evaluations of "1000 μm on" and "149 μm pass" are both rated "oo" or "o", the resultant particle size distribution becomes sharp and is regarded as acceptable. In contrast to this, either of the above-mentioned evaluations or both of them are rated "A" or "x", the resultant particle size distribution is not regarded as acceptable.

<Determination of Mean Particle Diameter of Powders of Less than 3 Mm>

In the above calculation, the opening of the sieve which first shows a mass frequency percent of 50% or more is supposed to be a (μm); the opening of the sieve next higher than the sieve having an opening of a (μm) is supposed to be b (μm); the cumulative finer mass frequency percent from the saucer to the sieve having an opening of a (μm) is supposed to be c (%); and the mass frequency percent on the sieve having an opening of a (μm) is supposed to be d (%). Then, the mean particle diameter (by mass-frequency percent of 50%) is determined according to the following formula:

$$\text{Mean particle diameter(by mass-frequency percent of } 50\%)=10^{(50-(c-d/\log b-\log a)\times \log b)/(d/(\log b-\log a))}$$

<Determination of Mean Particle Diameter of Flakes or Particles of 3 mm or More>

The axis having a maximum length of a flake or particle is supposed to be X; the axis of a cross section having a maximum length, perpendicular to the axis X is supposed to be Y; and the axis perpendicular to the two axes X and Y is supposed to be Z. The diameter obtained by averaging the total of the maximum length of X, the maximum length of Y and the length of Z axis is regarded as a characteristic diameter of one particle. The characteristic diameters of 50 or more flakes or particles are measured and the weight average particle diameter is obtained.

The raw materials used in Examples 26 to 30, 51 and 52, and Comparative Examples 18 to 22 are as follows:

Na carbonate: granular ash (made by Soda Ash Japan Co., Ltd.)

LAS-H: straight-chain alkylbenzenesulfonic acid (LIPON LH-200, made by Lion Corporation), having an AV value (the amount (mg) of potassium hydroxide required to neutralize one gram of LAS-H) of 180.0. In Table 5, LAS-H is expressed as LAS-Na that is obtained after neutralization with sodium hydroxide.

STPP: sodium tripolyphosphate (made by Taiyo Kagaku Kogyo)

Na Silicate: S50° sodium silicate No. 1 (made by Nippon Chemical Industrial Co., Ltd.) with a molar ratio of $SiO_2$ to $Na_2O$ of 2.15

Poly(Na acrylate): AQUALIC DL-453 (made by Nippon Shokubai Co., Ltd.) (in the form of an aqueous solution substantially containing 35 mass %)

Zeolite: Type-A zeolite (with a purity of 47.5 mass %) (made by Nippon Chemical Industrial Co., Ltd.)

Na sulfate: neutral salt cake, anhydrous (grade: A0) (made by Shikoku Chemicals Corporation)

Enzyme: SAVINASE 18T (made by Novozymes Japan)

Bleaching agent: sodium percarbonate, SPC-D (made by Mitsubishi Gas Chemical Company, Inc.)

Bleaching activator: granulated substance G of bleaching activator described in Examples of JP Kokai 2007-153596

Perfume: perfume composition containing: 0.5% of decanal, 0.3% of octanal, 10.0% of hexylcinnamyl aldehyde, 8.0% of dimethyl benzyl carbinyl acetate, 3.0% of lemon oil, 6.0% of lilial, 2.0% of lyral, 5.0% of linalool, 7.5% of phenylethyl alcohol, 2.0% of tonalid, 3.0% of o-tert-butyl cyclohexyl acetate, 2.0% of galaxolide BB*, 2.5% of linascol, 1.0% of geraniol, 2.0% of citronellol, 2.0% of jasmorange, 5.0% of methyl dihydro jasmonate, 1.0% of terpineol, 3.0% of methyl ionone, 5.0% of acetyl cedrene, 1.0% of lemonitrile, 1.0% of fruitate, 1.5% of orivone, 1.0% of benzoin, 0.5% of cis-3-hexenol, 2.0% of coumarin, 0.2% of damascenone, 0.3% of damascone, 1.5% of helional, 1.5% of heliotropine, 2.5% of anisaldehyde, 0.8% of gamma undecalactone, 1.2% of bacdanol, 0.5% of triplal, 1.5% of styrallyl acetate, 0.1% of calone, 3.0% of pentalide, 2.9% of oxahexadecen-2-on, and 6.2% of ethylene brassylate (*: benzyl benzoate)

In the above, the term "%" of each ingredient indicates the ratio by mass in the perfume composition.

The invention claimed is:

1. A solid fatty acid alkyl ester sulfonate metal sail, having an endothermic peak area between 50° C. and 130° C. which is at least 50% more than an endothermic peak area between 0° C. and 130° C. when determined using a differential scanning calorimeter, wherein the solid fatty acid alkyl ester sulfonate metal salt has a water content of 10 mass % or less, and the fatty acid alkyl ester sulfonate metal salt is represented by formula (1):

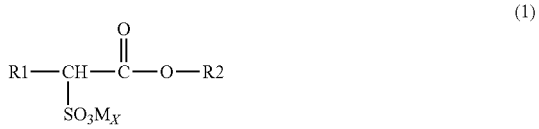
(1)

wherein $R^1$ is a straight-chain or branched alkyl or alkenyl group having 14 or 16 carbon atoms;
$R^2$ is a straight-chain or branched alkyl group having 1 to 4 carbon atoms;
M is an alkali metal ion or alkaline earth metal ion; and
X is 1 when M is an alkali metal ion, and ½ when M is an alkaline earth metal ion.

2. The solid fatty acid alkyl ester sulfonate metal salt of claim 1 further comprising 60 to 98 mass % of a fatty acid alkyl ester sulfonate metal salt, 1 to 10 mass % of an alkyl sulfate metal salt, and 1 to 10 mass % of a fatty acid sulfonate metal salt.

3. The solid fatty acid alkyl ester sulfonate metal salt of claim 1, wherein the fatty acid alkyl ester sulfonate metal salt is a mixture comprising a fatty acid alkyl ester sulfonate metal salt of formula (1); wherein R1 is a straight-chain or branched alkyl group or alkenyl group having 14 carbon atoms; and wherein the 14 carbon atoms of R1 are present in an amount of 40 mass % or more based on the total mass of the mixture.

4. The solid fatty acid alkyl ester sulfonate metal salt of claim 1 in the form of particles or flakes, wherein the particles or flakes have a mean particle diameter of at least 3 mm.

5. A method for producing the solid fatty acid alkyl ester sulfonate metal salt of claim 1, comprising:
(I) maintaining a metastable solid fatty acid alkyl ester sulfonate metal salt at 30° C. or more for at least 48 hours under pressure of 20,000 Pa or less, and at least one of
(II) melting a metastable solid fatty acid alkyl ester sulfonate metal salt to obtain a melt and maintaining the melt for 5 minutes or more at a temperature between a melting point of the metastable solid fatty acid alkyl ester sulfonate metal salt and a melting point of the solid fatty acid alkyl ester sulfonate metal salt, or
(III) melting a metastable solid fatty acid alkyl ester sulfonate metal salt to obtain a melt and applying a shearing force to the melt at a shear rate of at least 100 (1/s) or more at a temperature between a melting point of the metastable solid fatty acid alkyl ester sulfonate metal salt and 80° C.

6. A fatty acid alkyl ester sulfonate metal salt powder obtained by pulverizing the solid fatty acid alkyl ester sulfonate metal salt of claim 1.

7. A method for producing a fatty acid alkyl ester sulfonate metal salt powder comprising:

pulverizing the solid fatty acid alkyl ester sulfonate metal salt of claim 1 in a pulverizer, with an internal temperature of the pulverizer being adjusted to a range from 30° C. to 50° C.

8. The method of claim 7, wherein the solid fatty acid alkyl ester sulfonate metal salt is pulverized in the presence of an inorganic powder with a mean particle diameter ranging from 0.1 to 100 μm.

9. A fatty acid alkyl ester sulfonate metal salt powder obtained by pulverizing the solid fatty acid alkyl ester sulfonate metal salt of claim 1 in a pulverizer, with an internal temperature of the pulverizer being adjusted to a range from 30° C. to 50° C.

10. A granular detergent composition for textile goods or the dishes, comprising a fatty acid alkyl ester sulfonate metal salt powder of claim 6.

11. A method for producing the solid fatty acid alkyl ester sulfonate metal salt of claim 1, comprising:
maintaining a metastable solid fatty acid alkyl ester sulfonate metal salt at 30° C. or more for at least 48 hours under pressure of 20,000 Pa or less, and
melting a metastable solid fatty acid alkyl ester sulfonate metal salt to obtain a melt and maintaining the melt for at least 5 minutes at a temperature between a melting point of the metastable solid fatty acid alkyl ester sulfonate metal salt and a melting point of the solid fatty acid alkyl ester sulfonate metal salt.

12. A method for producing the solid fatty acid alkyl ester sulfonate metal salt of claim 1 comprising:
maintaining a metastable solid fatty acid alkyl ester sulfonate metal salt at 30° C. or more for at least 48 hours under pressure of 20,000 Pa or less, and
melting a metastable solid fatty acid alkyl ester sulfonate metal salt to obtain a melt and applying a shearing force to the melt at a shear rate of at least 1000 (1/s) at a temperature between a melting point of the metastable solid fatty acid alkyl ester sulfonate metal salt and 80° C.

13. A method for producing the solid fatty acid alkyl ester sulfonate metal salt of claim 3, comprising:
maintaining a metastable solid fatty acid alkyl ester sulfonate metal salt at 30° C. or more for at least 48 hours under pressure of 20,000 Pa or less, and
melting a metastable solid fatty acid alkyl ester sulfonate metal salt to obtain a melt and maintaining the melt for at least 5 minutes at a temperature between a melting point of the metastable solid fatty acid alkyl ester sulfonate metal salt and a melting point of the solid fatty acid alkyl ester sulfonate metal salt.

14. A method for producing the solid fatty acid alkyl ester sulfonate metal salt of claim 3, comprising:
maintaining a metastable solid fatty acid alkyl ester sulfonate metal salt at 30° C. or more for at least 48 hours under pressure of 20,000 Pa or less, and
melting a metastable solid fatty acid alkyl ester sulfonate metal salt to obtain a melt and applying a shearing force to the melt at a shear rate of at least 100 (1/s) at a temperature between a melting point of the metastable solid fatty acid alkyl ester sulfonate metal salt and 80° C.

15. A granular detergent composition for textile goods or the dishes, comprising a fatty acid alkyl ester sulfonate metal salt powder obtained by pulverizing the solid fatty acid alkyl ester sulfonate metal salt of claim 1.

16. A granular detergent composition for textile goods or the dishes, comprising a fatty acid alkyl ester sulfonate metal salt powder obtained by pulverizing the solid fatty acid alkyl ester sulfonate metal salt of claim 3.

* * * * *

UNITED STATES PATENT AND TRADEMARK OFFICE
CERTIFICATE OF CORRECTION

PATENT NO.         : 8,501,972 B2
APPLICATION NO.    : 12/739255
DATED              : August 6, 2013
INVENTOR(S)        : Yutaka Abe et al.

It is certified that error appears in the above-identified patent and that said Letters Patent is hereby corrected as shown below:

In the Claims:

- Claim 1, column 35, Line 7, after "sulfonate metal", and before "having"

Please replace "sail", with --salt--

Signed and Sealed this
Fifteenth Day of October, 2013

Teresa Stanek Rea
*Deputy Director of the United States Patent and Trademark Office*